(12) United States Patent
Novosselov et al.

(10) Patent No.: US 8,307,723 B2
(45) Date of Patent: Nov. 13, 2012

(54) PARTICLE INTERROGATION DEVICES AND METHODS

(75) Inventors: Igor V Novosselov, Seattle, WA (US); Peter C Ariessohn, Lake Tapps, WA (US); Evan D Dengler, Seattle, WA (US); Michelle Hickner, Seattle, WA (US)

(73) Assignee: Enertechnix, Inc., Maple Valley, WA (US)

( * ) Notice: Subject to any disclaimer, the term of this patent is extended or adjusted under 35 U.S.C. 154(b) by 354 days.

(21) Appl. No.: 12/834,860

(22) Filed: Jul. 12, 2010

(65) Prior Publication Data

US 2011/0132108 A1  Jun. 9, 2011

Related U.S. Application Data

(60) Provisional application No. 61/225,007, filed on Jul. 13, 2009, provisional application No. 61/318,313, filed on Mar. 27, 2010.

(51) Int. Cl.
*G01N 1/12* (2006.01)

(52) U.S. Cl. ............ 73/864.32; 73/864; 73/864.11

(58) Field of Classification Search .......... 73/864, 73/864.11, 864.32; 250/288
See application file for complete search history.

(56) References Cited

U.S. PATENT DOCUMENTS

| | | | |
|---|---|---|---|
| 3,970,428 A | 7/1976 | Barringer | |
| 4,580,440 A | 4/1986 | Reid | |
| 4,819,477 A | 4/1989 | Fisher | |
| 4,909,090 A | 3/1990 | McGown | |
| 5,092,218 A | 3/1992 | Fine | |
| 5,395,589 A | 3/1995 | Nacson | |
| 5,425,263 A | 6/1995 | Davies | |
| 5,465,607 A | 11/1995 | Corrigan | |
| 5,854,431 A | 12/1998 | Linker | |
| 6,073,499 A | 6/2000 | Settles | |
| 6,156,212 A | 12/2000 | Rader | |
| 6,334,365 B1 * | 1/2002 | Linker et al. | ............... 73/864.81 |
| 6,345,545 B1 | 2/2002 | Linker | |
| 6,523,393 B1 | 2/2003 | Linker | |
| 6,605,506 B2 | 8/2003 | Wu | |
| 6,828,795 B2 | 12/2004 | Krasnobaev | |
| 6,848,325 B2 | 2/2005 | Parmeter | |
| 6,861,646 B2 | 3/2005 | Motchkine | |
| 6,870,155 B2 * | 3/2005 | Krasnobaev et al. | ......... 250/283 |
| 6,887,710 B2 | 5/2005 | Call | |
| 6,906,322 B2 | 6/2005 | Berggren | |
| RE38,797 E | 9/2005 | Linker | |

(Continued)

FOREIGN PATENT DOCUMENTS

WO  2010095123  8/2010

*Primary Examiner* — David A. Rogers
*Assistant Examiner* — Rodney T Frank
(74) *Attorney, Agent, or Firm* — K Karel Lambert; Lambert Patent Services LLC

(57) ABSTRACT

Devices and methods are disclosed for non-contact pneumatic sampling of surfaces, persons, articles of clothing, buildings, furnishings, vehicles, baggage, packages, mail, and the like, for aerosols or vapor residues indicative of a hazard or a benefit, where the residues are chemical, radiological, biological, toxic, or infectious in character. A central orifice for pulling a vacuum is surrounded by an array of convergingly-directed gas jets, forming a "virtual sampling chamber". The gas jets are configured to deliver millisecond pneumatic pulses that erode particles and vapors from solid surfaces at a distance. A curtain wall flow encloses the sampling area during pulse retrieval.

17 Claims, 14 Drawing Sheets

U.S. PATENT DOCUMENTS

| | | |
|---|---|---|
| 7,141,786 B2 | 11/2006 | McGann |
| 7,208,122 B2 | 4/2007 | Swager |
| 7,275,453 B2 | 10/2007 | Ishikawa |
| 7,299,710 B2 | 11/2007 | Syage |
| 7,574,930 B2 * | 8/2009 | Bunker .................. 73/864.33 |
| 7,997,119 B2 * | 8/2011 | Wu ........................ 73/31.03 |
| 8,113,069 B2 * | 2/2012 | Settles .................... 73/864.35 |
| 2007/0158447 A1 * | 7/2007 | Bunker ................... 239/1 |
| 2009/0900840 | 4/2009 | Admirall |
| 2010/0062415 A1 | 3/2010 | Schwoebel |
| 2010/0252731 A1 | 10/2010 | Reilly |

* cited by examiner

300a

300b

300c

PARTICLE INTERROGATION DEVICES AND METHODS

CROSS-REFERENCE TO RELATED APPLICATIONS

This application claims the benefit of priority under 35 U.S.C. §119(e) from U.S. Provisional Patent Application No. 61/318,313 filed Mar. 27, 2010 and from U.S. Provisional Patent Application No. 61/225,007 filed Jul. 13, 2009; said priority documents being incorporated herein in entirety by reference.

GOVERNMENT SUPPORT

The United States Government may have certain rights in this invention pursuant to Grant No. HSHQDC-08-C-00076 awarded by the Department of Homeland Security.

FIELD AND BACKGROUND OF THE INVENTION

There is a need for non-invasive inspection and sampling of persons, articles of clothing, buildings, furnishings, vehicles, baggage, packages, mail, and the like for contaminating residues that may indicate chemical, radiological, biological or infectious hazards. Applications involve detection of trace materials, both particles and vapors, associated with persons who have handled explosives, detection of toxins in mail, or detection of spores on surfaces, while not limited thereto.

Current methods for environmental sampling often involve contacting use of swabs or liquids to obtain samples that are indicative of the composition of the environmental material of interest, but methods for sampling by "sniffing" are preferred. To inspect mail or luggage for example, the sampling method of U.S. Pat. No. 6,887,710 involves first placing the article or articles in a box-like enclosure equipped with airlocks, directing a blast of air onto the exposed surfaces in order to dislodge particles associated with the articles, then sampling the gaseous contents of the box by drawing any resulting aerosol through a sampling port. A similar approach for sampling persons is seen in U.S. Pat. No. 6,073,499 to Settles. Because any dislodged particles become dispersed in the larger enclosing space, very large volumes of air must be sampled in order to confidently ensure capture and analysis of any dislodged particles, and the process is inherently slow because each article or person must be moved into the box or chamber and the box sealed before sampling, an obvious disadvantage when large numbers of articles or persons must be screened, or when the articles are larger than can be reasonably enclosed, such as a truck, shipping container, or the hallway surfaces of a building.

Another technology is based on the luminescence of certain compounds when they attach to electron-rich explosive particles, and has been improved with the introduction of amplifying fluorescent polymers as described in U.S. Pat. No. 7,208,122 to Swager (ICx Technologies, Arlington Va.). Typically vapors are introduced into a tubular sensor lined with a conductive fluorescent polymer by suction. However, the suction intake inherently draws in air that has not contacted the article or surface of interest, even when held very close while sampling, and no provision is made for resuspending particles or vapor residues associated with the target surface. Furthermore, these sensors also lack a pre-concentrator and work only for analytes with electron-donating properties.

Another common analytical instrument for detection of nitrate-type explosives relies on pyrolysis followed by redox (electron capture) detection of $NO_2$ groups (Scientrex EVD 3000), but is prone to false alarms. Ion mobility spectroscopic (IMS) detectors are in widespread use and typically have picogram sensitivity. IMS also requires the ionization of the sample, which is typically accomplished by a radioactive source such as Nickel-63 or Americium-241. This technology is found in most commercially available explosive detectors like the GE VaporTracer (GESecurity, Bradenton, Fla.), the Sabre 4000 (Smiths Detection, Herts, UK) and Russian built models. The requirement for a radioactive ionization source may limit their use.

Other analytical modalities are available. However, all such instruments can benefit from a portable "front end" device for sampling of vapors and particles associated with surfaces. In particular, there is a need for a front end device that can be directed to dislodge particles and residues from target surfaces and concentrate them before presentation to the analytical instrument of choice, an approach that optimizes sensitivity and can speed deployment because the need to enclose the target surface in a sealed chamber is avoided.

The preferred devices, systems and methods overcomes the above disadvantages and limitations and are portable and sensitive in detecting hazardous particles or vapors on the external surfaces of objects, structures, vehicles or persons.

SUMMARY

Disclosed is a pneumatic sampling head with "virtual sampling chamber" for sampling hazardous contaminants such as traces of explosives, infectious agents, or toxins on persons, articles of clothing, buildings, furnishings, vehicles, baggage, packages, mail, and the like. The system includes a sampling head with a central collection intake operated under suction and surrounded by an annular array of jet nozzles directed convergingly toward the apex of a virtual cone extending from the sampling head. The virtual sampling chamber is formed when streamlines of gas discharged by the jet nozzle array impinge on an external surface. The jets serve to dislodge particulate and vapor residues on a surface and the suction intake draws them into the sampling head.

Surprisingly, gas jets operated in a millisecond-scale pulse mode are found to be more effective than gas jets operated continuously in collecting particulate and vapor residues with the sampling head. The virtual sampling chamber may be formed and collapsed in less than a second in response to a single synchronized pulse, or may be formed intermittently, such as by a train of synchronized pulses separated by a fraction of a second or longer, during operation. The sampling head may be compact for portable hand-directed operation or scaled up and operated robotically for screening of vehicles and cargo containers, while not limited thereto.

In a first embodiment, the device is a pneumatic sampling head for sampling residues, including particulate and vapor residues, from an external surface of an object, structure, vehicle or person, which comprises a) a sampling head with forward face and perimeter; b) a suction intake port disposed centrally on the forward face and an array of jet nozzles peripherally disposed on the forward face around the suction intake port, wherein the jet nozzles are directed at a virtual apex of a virtual cone with base resting on the forward face; c) a positive pressure source for firing or propelling a gas sampling jet or stream with streamlines from each nozzle of the array of jet nozzles; d) a suction pressure source for drawing a sampling return stream of gas into the suction intake port, the suction pressure source having an inlet and an outlet; where the streamlines of the gas sampling jet pulses are directed toward the virtual apex of the virtual cone, the streamlines tracing an involuted frustroconical "U-turn" under the attraction of the suction pressure source and converging with the sampling return stream at the suction intake port along a central axis of the virtual cone when impinging on the external surface.

The out-flow of the gas sampling jets and in-flow of the sampling return stream form a "virtual sampling chamber" with the gas sampling jet pulses directed linearly along the walls of the virtual cone toward its apex and the sampling return stream directed along the central axis of the virtual cone toward its base, and further wherein the involuted frustroconical "U" fluidly connects the gas sampling jets and the sampling return stream at a virtual frustrum when impinging on an external surface. In preferred embodiments the device is operative at up to 1 foot from the external surface.

Surprisingly, we have found that pneumatic pulses or streams emitted from a concentric array of gas interrogation jet nozzles directed in trajectories along the walls of a virtual cone will turn inward when directed at a surface and return to a common suction intake port mounted in the sampling head in the center of the jet array. The sampling head may be held at a distance and aimed at the surface to be interrogated. Targetable jet nozzles and laser guidance may be used to shape the pulse geometry if desired. Particles or vapors removed from the interrogated surface do not escape the "virtual sampling chamber" and are taken up through the suction intake, where they may then be concentrated and analyzed by a variety of methods.

In one embodiment, multiple circumferentially disposed interrogation jets angled downward from a common sampling head emit pneumatic pulses that converge toward a common focal point but are bent back on themselves when encountering an external surface and are collected in a central collection duct operated under suction pressure. The pneumatic pulses initially follow directional vectors converging along the walls of a "virtual cone", but upon contact with a surface disposed at a distance from the base of the cone $D_f$ which is less than the height of the cone $D_c$, a virtual frustrum is formed by involution of the streamline vectors so that the streamlines flow back along the central axis of the cone into an intake duct centrally mounted on the face of the sampling head. The virtual cone thus becomes a closed "virtual sampling chamber" where objects or surfaces brought within the cone are stripped of volatiles and loose particulates and carried into the sampling head. Once entrained in the suction intake, particles or vapors in the stream of air may be concentrated for collection or analysis.

Sampling jet and suction intake gas flows may be discontinuous or continuous, balanced or imbalanced, subsonic or sonic in character. In one embodiment, the in-flows and out-flows from the sampling head are equal and opposite and form a closed loop, so that vapors or particles not trapped in the sampling head are recirculated and accumulate in the loop. In another embodiment, the jet pulse out-flow is powered by an independent pressure source and is exceeded by the suction in-flow to achieve a net positive sampling, such as when a millisecond sampling pulse out-flow is followed by a suction in-flow of longer duration.

In practice, it has proved useful to operate the gas jets in pulse mode or pulse train mode. In pulse mode, the gas jets fire as a short burst after first activating the suction intake. In pulse train mode, a series of short bursts are emitted from the gas jets while operating the suction intake. A surface or object may be sampled with a single pulse or with a series of pulses. The sampling head may be moved or stationary between pulses, or a series of pulses may be emitted while the sampling head is moving.

In a second embodiment, the array of interrogation jet nozzles is surrounded by a perimeter of circumferential slits that emit a curtain wall of lower velocity gas forming an apron around the virtual cone of the higher velocity convergent jets. This air is conveniently supplied by the exhaust of the suction intake. The exhaust of a blower used to power the suction intake, for example, may also be used to provide the gas flow for the curtain wall.

In another embodiment, the invention is a method for sampling a residue from an exterior surface of an object, structure or person, which comprises contacting a virtual sampling chamber as described herein with an exterior surface at a distance less than the height $D_c$ of the virtual cone, whereby residues dislodged from the external surface by the gas jets are swept into a sampling return stream by the suction intake. The virtual sampling chamber may be employed intermittently with triggering, cyclically, or continuously.

Our approach to a pneumatic sampling head combines biomimetic "sniffing" and interrogation jets, serving as a front end particle and vapor residue concentrator and capture device for use with a variety of analytical tools and instruments. These sampling heads may be interfaced with particle or vapor collection and analysis systems for detection of trace residues associated with explosives, particles associated with biowarfare agents, residues or particles associated with narcotrafficking, environmental contamination of surfaces with toxins, bacterial or other contamination in food processing facilities, and so forth. These systems are thus part of larger surveillance systems of use in surveillance of complex environments, such as traffic at the border, flow of mail, ingress and egress of persons from secure areas, and in forensic investigations, for example. Such systems may also be used in process control applications.

BRIEF DESCRIPTION OF THE DRAWINGS

The teachings of the present invention can be readily understood by considering the following detailed description in conjunction with the accompanying drawings, in which.

DETAILED DESCRIPTION

Figure 1A:
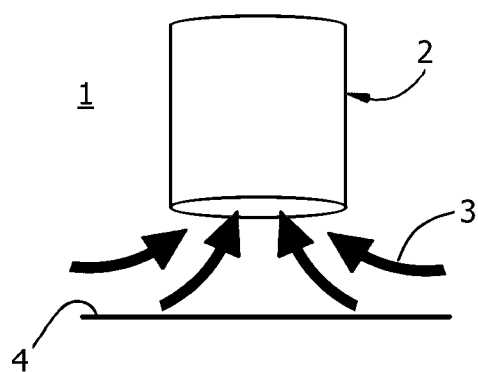
FIGS. 1A and 1B are schematics showing devices of the prior art.

Although the following detailed description contains many specific details for the purposes of illustration, one of skill in the art will appreciate that many variations, substitutions and alterations to the following details are within the scope of the invention. Accordingly, the exemplary embodiments of the invention described below are set forth without any loss of generality to, and without imposing limitations upon, the claimed invention.

The invention has applications for surveillance and analysis of particulates and volatile residues borne upon persons, articles of clothing, interior or exterior surfaces of buildings, furnishings, vehicles, baggage, packages, mail, and so forth. Particulate and volatile residues include a variety of analytes, such as chemical agents, explosives residues, radiological agents, biological agents, toxins and narcotics.

Explosive residues may be found not only on environmental surfaces, but also on persons. Persons handling explosives often transfer these residues onto surfaces which may later be intercepted. Explosives include trinitrotoluene (TNT), nitroglycerine, dinitroglycerine, cyclonite (hexahydro-1,3,5-trinitro-1,3,5-triazine, RDX), pentaerythritol tetranitrate (PETN), 1,3,5-triamino-2,4,6-trinitrobenzene (TATB), triacetone triperoxide (TATP), ammonium nitrate, urea nitrate, ANFO (ammonium nitrate/fuel oil mixtures), for example, while not limited thereto. Because volatile molecular species such as ethylene glycol dinitrate (EGDN), dimethyldinitrobutane, mononitroluene, or isotopically labeled explosives are used for "tagging" commercial explosives as a means of source identification, these are also of use for detection (Steinfeld J I and J. Wormhoudt. 1998. Explosives detection: a challenge for physical chemistry. Ann Rev Phys 49:203-32). Also of interest as targets for detection are those agents identified and listed by the Bureau of Alcohol, Tobacco and Firearms as explosives under section 841(d) of Title 18, USC. Firearms residues may also be encountered.

Also targets are chemical agents such as tabun (GA), sarin (GB), soman (GD), cyclosarin (GF), and VX (methylphosphonothioic acid); blister agents such as sulfur mustard, nitrogen mustard, Lewisite, and phosgene oximine; choking agents such as phosgene, diphosgene, chlorine and chloropicrin, lacrimators such as chlorobenzylidene-malononitrile, chloroacetophenone, and nitrochloromethane; herbicides such as "agent orange" and Round-up® organophosphates, pesticides such as Isotox®, Procure®, Fluvalinate, Imidacloprid, Coumaphos, Apistan®, CheckMite®, Aldicarb®, Neonicotinoids, Pyrethroids, and Gaucho®, for example, as may also be encountered in residues deposited on persons, objects, or on environmental surfaces.

Biological particulate agents include *Staphylococcus enterotoxin B*), bacteria (including *Bacillus anthracis*, *Brucella melitensis*, *Brucella abortus*, *Bordatella pertussis*, *Bordatella bronchioseptica*, *Burkholderia pseudomallei*, *Pseudomonas aeruginosa*, *Pseudomonas putrefaciens*, *Pseudomonas cepacia*, *Eikenella corrodens*, *Neisseria meningitides*, *Corynebacterium diptheriae*, *Fusobacterium necrophorum*, *Mycobacterium tuberculosis*, *Actinobacillus equuli*, *Haemophilus influenzae*, *Klebsiella oxytoca*, *Klebsiella pneumoniae*, *Legionella pneumophila*, *Listeria monocytogenes*, *Kingella denitrificans*, *Coxiella burnetii*, *Yersinia pestis*, *Pasteurella multocida*, *Vibrio cholera*, *Streptococcus pyogenes*, *Francisella tularensis*, *Francisella novicida*, *Moraxella catarrhalis*, *Mycoplasma pneumoniae*, *Streptococcus pneumoniae*, *Staphylococcus aureus*, methicillin-resistant *Staphylococcus aureus* (MRSA), and *Vibrio cholera*), *Rickettsia* (including *Chlamydia pneumoniae*, *Chlamydia trachomatis*, *Rickettsia prowazekii*, and *Rickettsia typhi*), and viruses (including Western Equine Encephalitis virus, Eastern Equine Encephalitis virus, Venezuelan Equine Encephalitis virus, Enteroviruses, Influenza virus, bird flu, Coronavirus, Adenovirus, Parainfluenza virus, Hanta virus, Argentine Hemorrhagic Fever virus, Machupo virus, Sabia virus, Guanarito virus, Congo-Crimean Hemorrhagic Fever virus, Lassa Hemorrhagic Fever virus, Marburg virus, Ebola virus, Rift Valley Fever virus, Kyasanur Forest Disease virus, Omsk Hemorrhagic Fever, Yellow Fever virus, Dengue virus, Smallpox virus, Monkeypox virus, and foot and mouth disease virus), among others, fungal agents such as *Coccidiodes immitis*, *Candida albicans*, *Cryptococcus neoformans*, and *Aspergillus fumigatus*, and may also include plant pathogens of economic significance such as citrus canker and rust viruses of grains.

Putative toxins that may be encountered include innocuous "white powders", and Botulinum toxin, Diptheria toxin, Tetanus toxin, Staphylococcal enterotoxin B, saxitoxin, tetrodotoxin, palytoxin, brevetoxin, microcystin, Trichothecene mycotoxins (eg. T2), diacetoxyscirpenol, nivalenol, 4-deoxynivalenol, cereulide, ricin, and *Yersinia pestis* F1 antigen, for example, while not limited hereto.

Turning now to the figures, a conventional vacuum sampling device (1) with intake (2) is shown schematically in FIG. 1A. Under influence of suction pressure applied to the intake, flow streamlines (3) enter the intake port from the sides, sweeping across a proximate external surface (4) and picking up loose particles, but the devices have a reduced sensitivity due to dilution with ambient air.

Figure 1B:
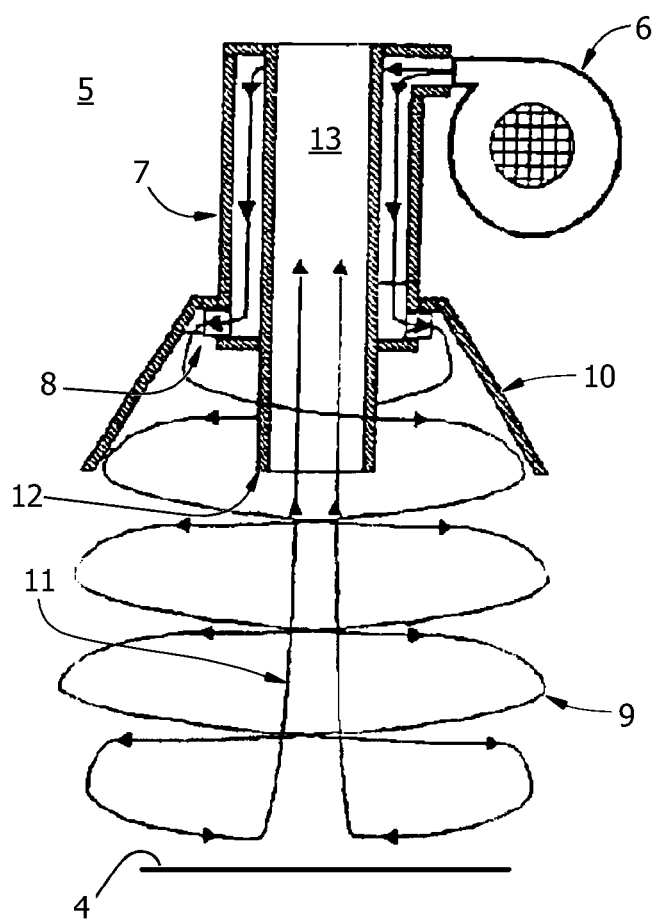

As described in U.S. Pat. No. 6,861,646, application of a cyclonic outer flow regime is reported to improve the ability to sample complex surfaces at a distance from the detector head. This is shown schematically in FIG. 1B. A blower (6) powers outflow of cyclonic streamlines (9) through lateral port (8) in housing (7). A bonnet (10) is used to shape the cyclone. A central vacuum intake (13) draws air from the base of the cyclone. Inflow streamlines (11) are seen to rise into the vacuum intake. An external surface (4) is shown to be swept by the cyclonic streamlines (9) and dislodged materials are entrained in the returning gas flow (11). Because the cyclonic streamlines (9) engage the external surface (4) at an essentially zero incidence angle, particle rolling is favored over particle detachment. In contrast, we have directed jet pulses or streams converging toward a virtual apex of a cone behind the surface to be interrogated. Cyclonic flow of the incident air stream is not believed relevant to the operation of our invention. We have found that for particle removal the impingement or incidence angle of a jet streamline, i.e. the angle of the streamline relative to a flat surface generally parallel to the sampling head, exhibits improved dislodgement and aspiration efficiency at about 60 degrees or higher. In contrast, in the cyclonic flow regime of the art, cyclonic streamlines are essentially parallel to the surface and the incidence angle approaches zero.

FIG. 2A depicts a "virtual sampling chamber" (250) of the present invention formed of six jets of air emitted from sampling nozzles arrayed around a generally central suction intake port. The sampling jets are directed to form the walls of a virtual cone, shown here converging on an interrogated surface (4). When incident against the interrogated surface, the jets involute and are borne into the central collection duct in the sampling head. In this way, particles or vapors dislodged or volatilized from the interrogated surface are entrained in the returning flow and enter the suction intake port for concentration and analysis.

In more detail, for a first embodiment (200) of the invention, sampling head (210) has a forward face (211) and a ring of jet nozzles (212) mounted in a circumferential array around a central axis (214). At the center of the forward face is a suction intake port (213) with conical inlet. Sampling jets (220) propelled from the jet nozzles (212) are directed to converge on an external surface (4), forming the walls of a truncated virtual cone. On striking the surface, the jets are turned inward and are returned under suction to the suction intake port (213). Suction is generated by a vacuum pump (or blower inlet) mounted in or connected to the sampling head. A bundled core of suction return streamlines (230) is shown at the central long axis of what is a "virtual sampling chamber" (250), the virtual sampling chamber having a truncated conical shape with base formed by the forward face (211) of the sampling head and frustrum by out-flow streamlines making an involuted frustroconical "U" turn (221) on the interrogation surface (4). The frustroconical "U" turn of the out-flow streams at the frustrum fluidly joins the out-flowing gas jets (220) with the bundled in-flowing return streams (230) directed into the suction intake.

Also shown is a positive pressure source (240), here a diaphragm pump, for charging the gas jets and tabulation (246) for discharging a curtain wall flow through annular slit orifices (245) disposed as an apron around the sampling head, as will be discussed further below.

The geometry of the conical "virtual sampling chamber" (250) is illustrated schematically in FIG. 4. The virtual cone geometry (351) includes base (352), with central long axis (214), walls (353), apex or vertex (360), and frustrum (354). The walls of the virtual sampling chamber are formed by jets (220) flowing down the outside walls of cone from the base to the apex. Returning flow (230) is formed by involution of the jets (220) where the cone is truncated on the frustrum. While not bound by abstract models, the returning flow is visualized as a cylinder (355) of negative pressure having a base (356) at the core of—and disposed on the long axis of—the virtual cone. An involuted frustroconical "U-turn" of the gas flow streamlines fluidly joins the gas jets (220) to the sampling return stream (230). The number of jets forming the virtual sampling chamber may be two, three, four, six, eight, or more, while not limited thereto. By shaping the jet streamlines (220) in fan or chisel shapes, a virtual cone or pyramid is readily formed with as few as two shaped jets.

As discussed further below, the sampling jets may be emitted as pulsed bursts, and after an interval of a few microseconds, the emitted gas is recovered by application of a strong suction pulse. Thus it can be seen that the gas-walled sampling chamber is formed and then collapses—truly an evanescent manifestation of a virtual sampling chamber having a duty cycle of a few seconds, while not limited thereto.

Although not shown, the source of pressurized gas for the sampling jets and vacuum for the suction intake may include centrifugal, rotary vane, piston, or diaphragm pumps, or other pumps as known in the art. The exhaust of the suction gas generator may be used to drive the gas jets of the out-flow. A high pressure tank of a gas or pressure reservoir may be charged to a pressure setpoint and gas released using high-speed solenoid valves to generate sampling jet pulses. An outermost peripheral annular curtain wall flow may also be used to further enclose the virtual sampling chamber, as will be described below.

Average jet flow velocities in the range of 20 to 300 m/s have been found useful in studies performed to date. Supersonic jets may also be used. The calculated average jet velocity at the outlet of a nozzle for smaller diameter nozzles approaches 300 m/s, which indicates that the velocity at the nozzle center line is sonic, and that it operates at choked conditions with higher then ambient air density. Modeling studies by computational fluid dynamics show that jet velocities and suction pressure diminish over distance from the sampling nozzle, but are capable of forming a virtual sampling chamber enclosing a distance $D_f$ of up to about 12 inches or more from the interrogated surface, where the distance $D_f$ is the height of a frustrum of a virtual cone as measured from its base (FIG. 4). In operation, the height of the virtual cone from base to apex is $D_c$, the virtual frustrum is formed with a height $D_f$, where the height $D_f$ is less than $D_c$. The distance $D_f$ may be 1 inch, 3 inches, 6 inches, 12 inches, or as found suitable for particular applications, according to the power of the jet pulses or streams.

The apex angle "theta" (or "vertex angle") of convergence of the jets forming the virtual cone may be varied as desired, but is found to be more effective in the range of 10 to 60 degrees, most preferably about 15 degrees. For a normal jet, the incidence angle is the external angle of the half angle of theta. In some applications, in order to increase the standoff distance $D_c$, it may be desirable to use a jet that approaches normal to the forward face of the sampling head. Instead of a virtual cone, a virtual sampling chamber that is generally cylindrical can be formed when the jets are parallel in trajectory.

A system having negligible losses outside the virtual sampling chamber is formed by balancing in-flow suction and out-flow jet emission in one embodiment and in another embodiment by increasing the in-flow suction ratio. When in-flow and out-flow are balanced, a system may be operated as a closed loop. In other embodiments, an open-loop is formed by firing the jets from a pressurized reservoir and ducting the sampling return stream through a blower to charge the curtain wall flows.

FIG. 2B is a face view of the underside of a sampling head (200), termed herein the forward face (210). In this view, the forward face is generally round, but is not limited thereto. Depicted are peripherally disposed gas jet nozzles (212) and annular slits (245) used for curtain wall flow. Within the bell of the sample intake port (213, FIG. 2C), is a suction inlet (216) which is ducted to a suction pressure source (not shown). Also shown is the cross-sectional plane of the view of the sampling head of FIG. 2C.

Figure 2A:
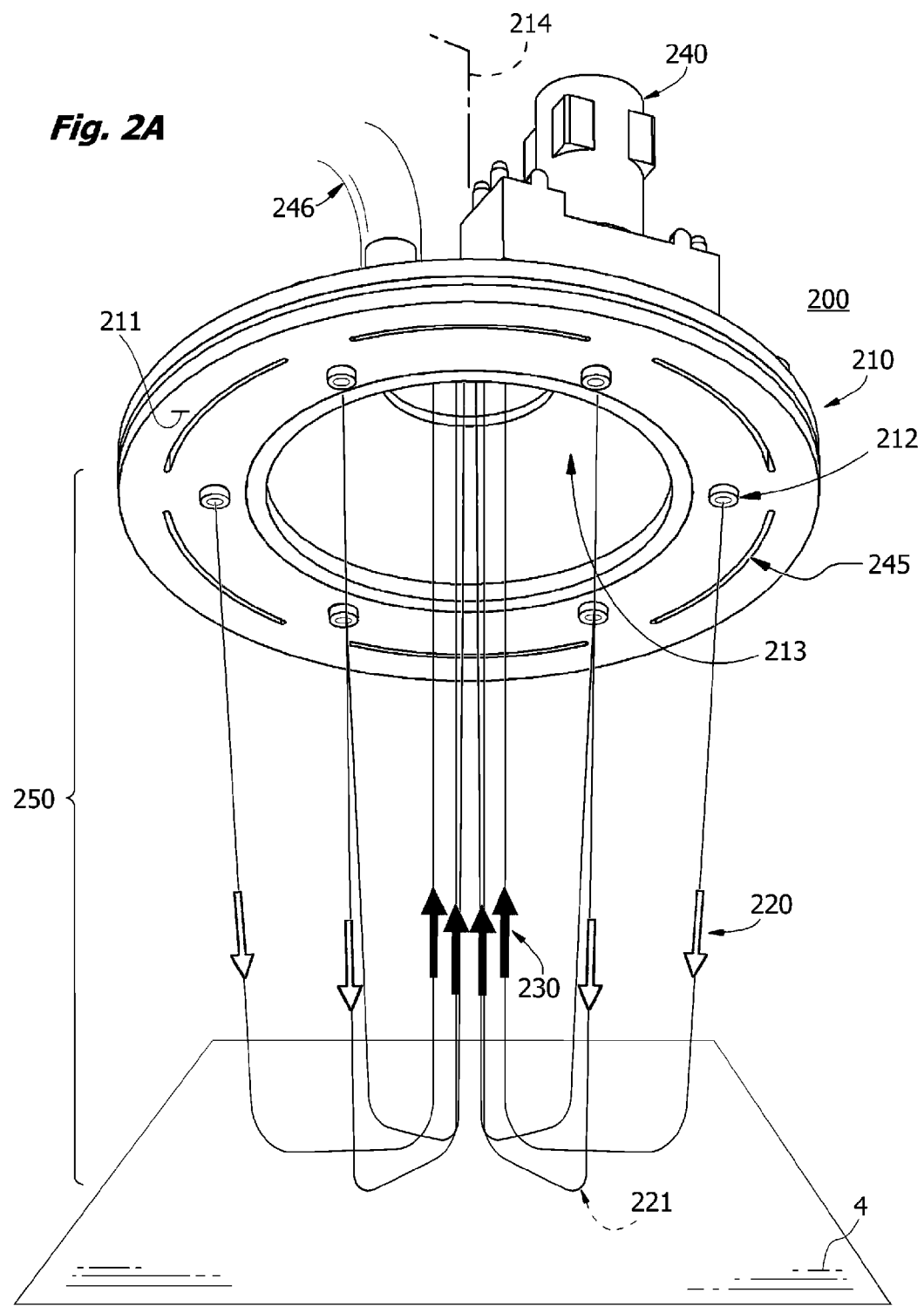
FIG. 2A is schematic depiction of a sampling head in operation, the sampling head having six sampling jets surrounding a central intake port. A "virtual sampling chamber" is formed.
Figure 2B:
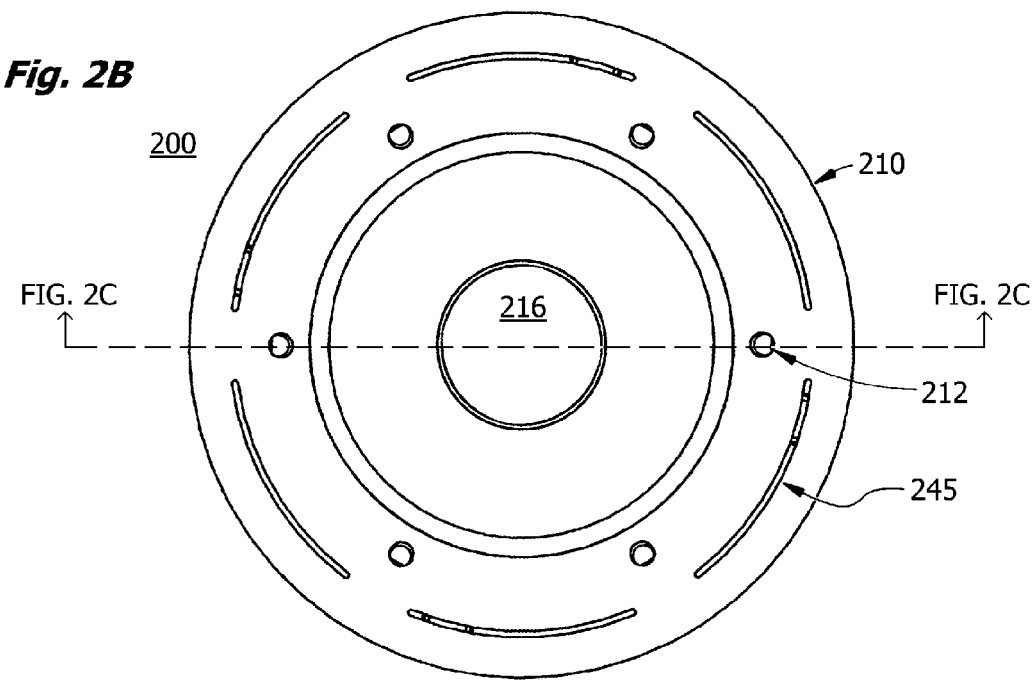
FIGS. 2B, 2C and 2D depict plan, section and elevation views of the six jet sampling head of FIG. 2A.
Figure 2C:
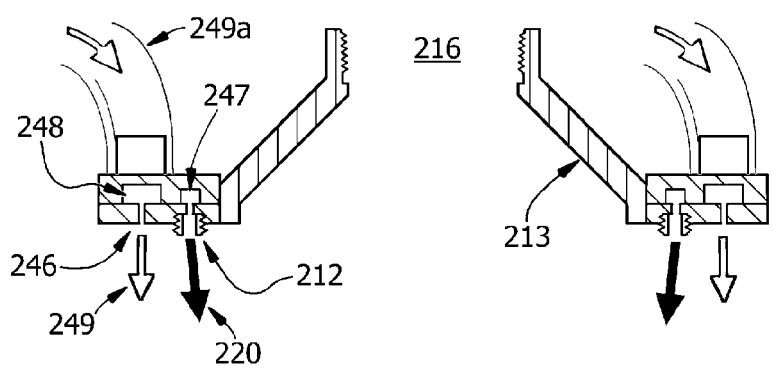

FIG. 2C is a cross-sectional view of sampling head (200). The suction intake port (213) is depicted as being conical, but is not limited thereto, and is shown here with a threaded suction inlet (216) for connecting to a negative pressure source. The central inlet is bounded by a plate for mounting the gas jet nozzles (212) represented by a black arrow (220) and containing the annular slits (246) use for curtain wall flow represented by an open arrow (249). Internal to the plate are distribution manifolds, a first plenum (247) for supplying pressurized gas to the jet nozzles (212) and a second plenum (248) for distributing make-up gas to the curtain wall slits (246). In this embodiment, the curtain wall flows (249) are supplied from a blower via tubulations (249a) and curtain wall plenum (248).

Figure 2D:
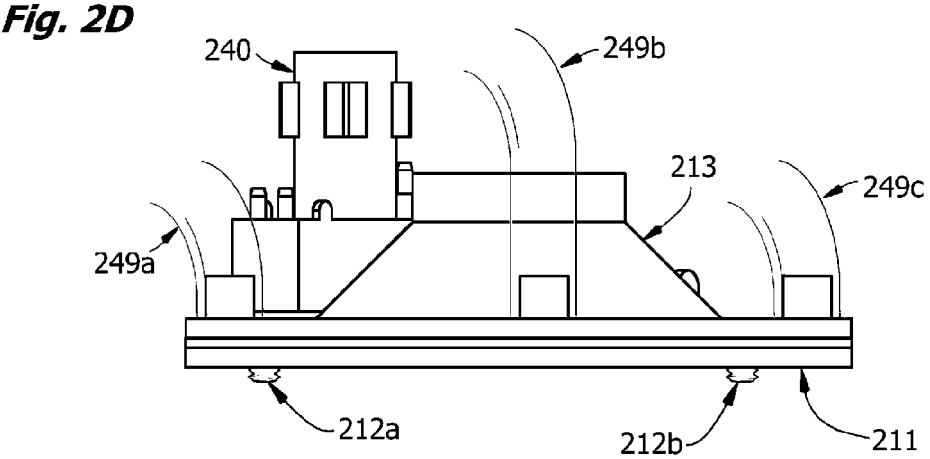

FIG. 2D depicts a corresponding plan view. Shown is the conical shape of the suction intake port (213, external view), the flat forward face (211) of the sampling head, gas jets (212a,212b) mounted in the forward face, tabulations for supplying curtain wall flow (249a,b,c), and a diaphragm pump (240) depicted earlier, which supplies pressurized air to the gas jet plenum (247) in this embodiment.

Figure 3A:
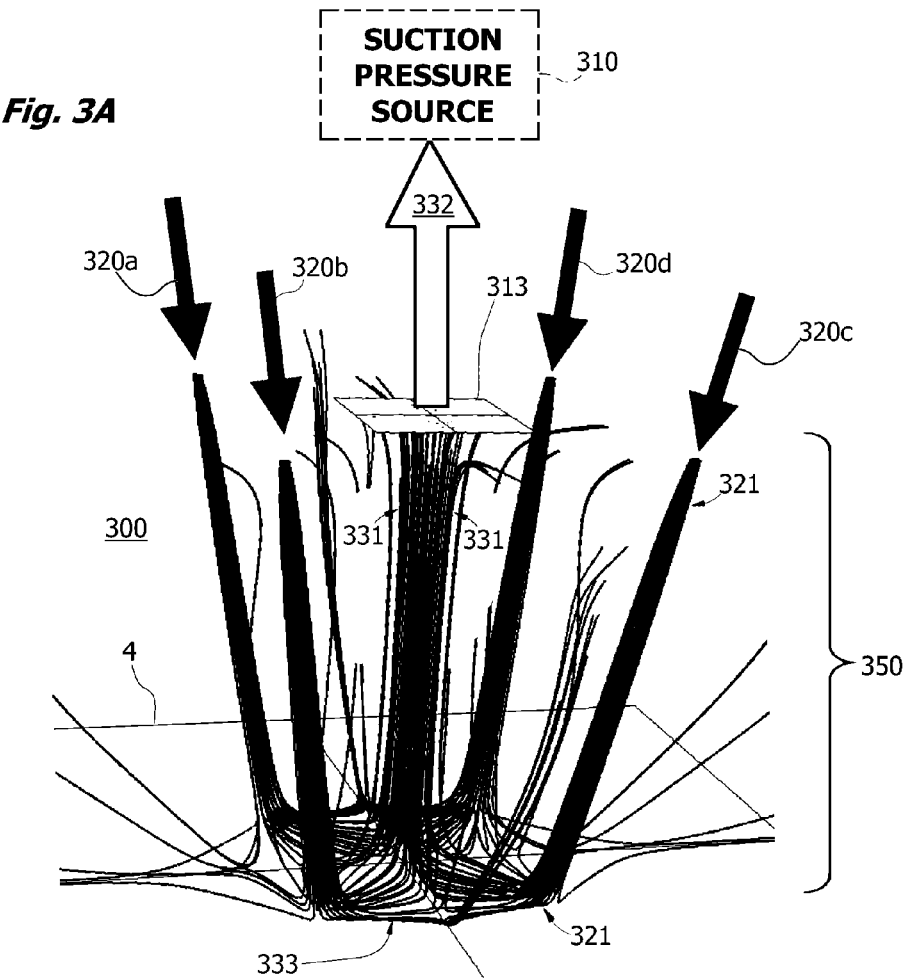
FIG. 3A is a computational model of a four-jet virtual sampling chamber formed by a sampling head of a device of the invention. The lines represent streamlines of air.
Figure 3B:
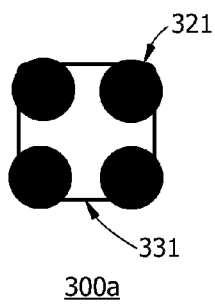
FIGS. 3B through 3D depict the footprint on the interrogated surface established by various configurations of jets, showing quad-, tri- and octa-jet configurations.
Figure 3C:
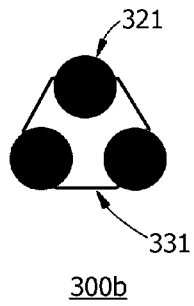
Figure 3D:
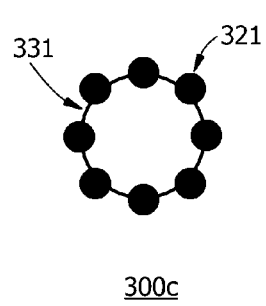

A computational fluid dynamics (CFD) model (300) of the pneumatic action of a sampling head with four jets (320a, 320b,320c, 320d) is shown in FIG. 3A. With the exception of suction intake port (313) and suction pressure source (310), the mechanics of the device itself are not shown so that the pneumatic streamlines can be more readily visualized. The four sampling jets are directed downward at a surface (4) so that the jets converge slightly in proximity to the surface. The out-flow jet streamlines (321) surround a virtual sampling chamber (350). A suction return stream (332, formed by bundled parallel in-flow streamlines 331) is shown directed upward within the core of the virtual sampling chamber. Out-flowing jet streamlines (321) bend at the base, involuting as a frustroconical "U" shaped squarish toroid (333) where contacting the external surface (4). As shown by CFD, vortex cyclonic flow does not develop under these conditions. FIGS. 3B through 3D represent figuratively the 'footprint' of the jet out-flow streamlines (321) and suction in-flow streamlines (331) on an interrogated external surface for three, four and eight jet configurations.

In contrast to the prior art, we have directed the sampling flow as generally convergent jet pulses or jet streams toward the apex of a virtual cone, where the apex of the imaginary cone is behind the surface to be interrogated. In preliminary work, the impingement or incidence angle of a linear streamline forming the walls of a virtual sampling chamber is most effective for residue dislodgement and aspiration at about 5 to 30 degrees from normal, which cannot be achieved in a cyclonic flow regime, where streamlines are essentially perpendicular to the bulk axis of flow and the impingement angle approaches zero. At lower impingement angles, rolling and sliding of particles is favored over lift-off The higher impingement angle permits the use of higher intensity focused jets and the application of pulsatile sonic and supersonic flow regimes, which results in lift-off and removal of both particulate and volatile materials from irregular and complex surfaces, and in better re-aerosolization and aspiration of particles.

By balancing the "out-flow" of the jet nozzles and the "in-flow" of the suction intake, a closed loop may be formed in which sample residues are concentrated over multiple passes through a vapor or particle trap. A shroud or cowling may optionally be used to shape the outlet and intake gas flows. The sampling device is intended for particle and vapor removal and for aspiration of dislodged particles and vapors into the sample head from surfaces or objects from a distance $D_f$ of up to about 1 foot, for example a vehicle driven between stanchions supporting sampling devices directed at intervals onto the surfaces of the vehicle. The size and power of the jets and suction intake can be scaled for larger standoff distances if needed.

While configurations with four jets, six jets and eight jets are shown, other configurations and numbers of jets are envisaged. In selected geometries, a three-jet or a two jet sampling head, where the jets are fan shaped, is directed at a surface and a mated central suction intake is configured to capture materials ejected from the surface by the impinging jets, optionally with a curtain wall or apron of flowing air improve containment. Other variants for establishing a virtual sampling chamber are possible and are not enumerated here.

Figure 5:
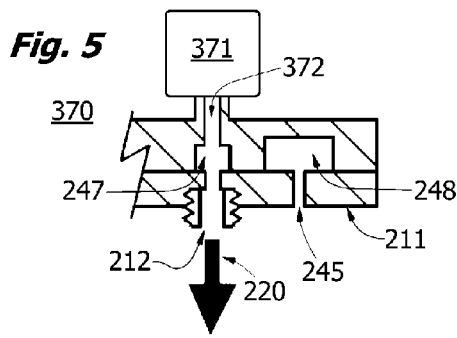
FIG. 5 shows a detail of solenoid valve control of a gas interrogation jet in a sampling head.
Figure 4:
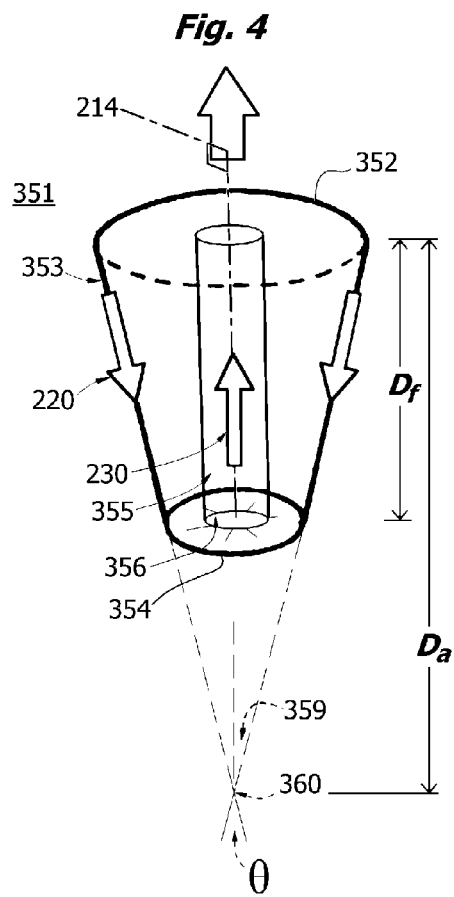
FIG. 4 is a pictographic representation of the geometry of a virtual sampling chamber.

FIG. 5 depicts a detail of solenoid valve control of a gas interrogation jet in a sampling head. Jet control assembly (370) includes solenoid valve (372, control wiring not shown), and jet gas supply duct (371) fluidically connected to the jet plenum (247). Gas supplied to the plenum is rapidly distributed through the plenum manifold to all jet nozzles in the array. The array of jet nozzles is fired in synchrony. A jet pulse (220) is schematically depicted exiting jet nozzle (212) mounted on the forward face (211) of the sampling head. Also shown is curtain wall plenum (248) and curtain wall orifice (245). The curtain wall may be operated continuously or operated intermittently under solenoid control.

Figure 6:
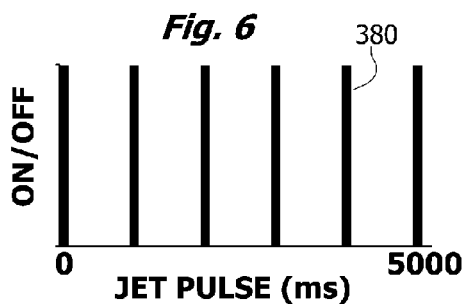
FIG. 6 represents a pulse train of gas jets firing in synchrony.

FIG. 6 represents a pulse train of gas jets firing in synchrony over a period of 5000 milliseconds. Each gas jet pulse (380) originates as a pressurized wave of gas equilibrated through plenum (247) and discharged through an array of nozzles (212). Gas jet pulses are followed by a period of suction to capture materials dispersed in the virtual sampling chamber by virtue of the impact of the gas jet or shock wave on the external surface. During the suction part of the cycle, make up air may be supplied from the surrounding air column or from an optional curtain wall flow. While gas jet flow may be operated continuously, in practice this has not proved necessary, and discontinuous application of jet pulses with a limited duty cycle may be advantageous. In one method of practice of the invention, sampling jet pulses as fired as synchronous pulses or as a train of synchronous pulses having a pulse duration of less than or about 200 microseconds, thereby intermittently forming a virtual sampling chamber on the surface of a surface to be interrogated for volatile residues or particulate matter.

Figure 7:
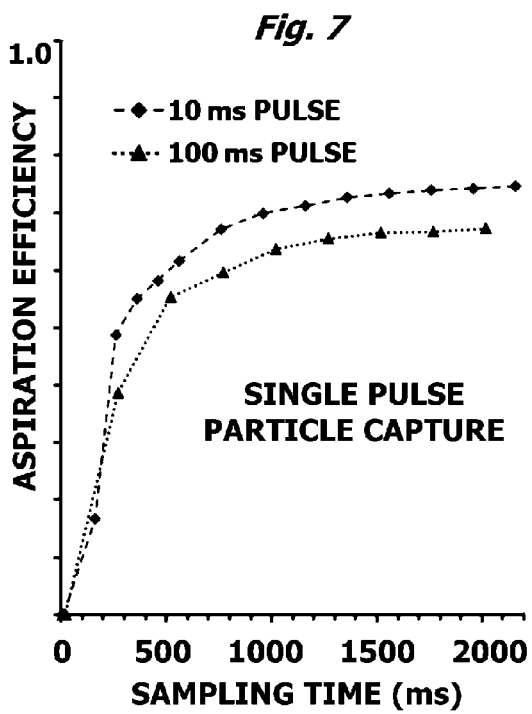
FIG. 7 is a plot showing single pulse particle aspiration efficiency $\eta_A$ as a function of pulse duration in an eight jet device.
Figure 8:
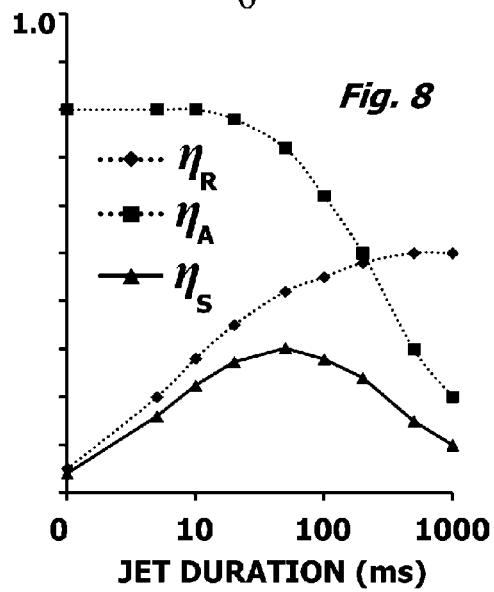
FIG. 8 is a plot showing particle sampling efficiency $\eta_S$ as a function of jet pulse duration.
Figure 9:
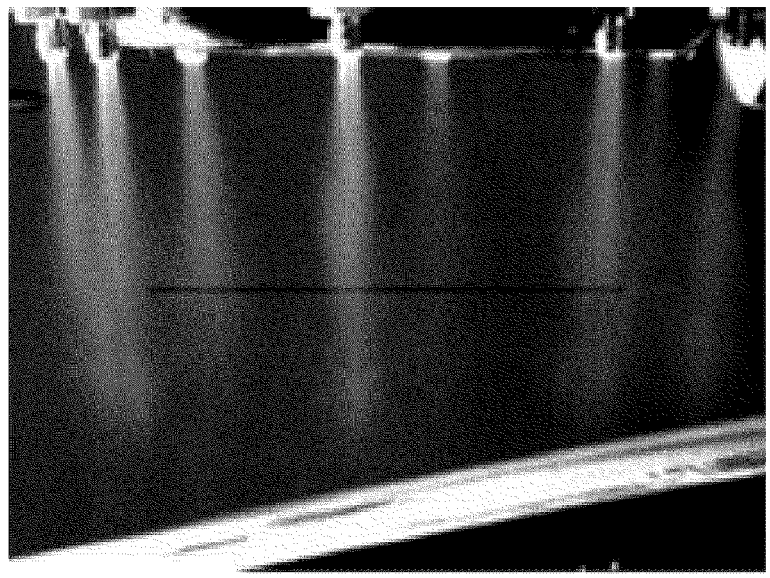
FIG. 9 is a pictogram depicting firing of an eight-jet device.
Figure 10:
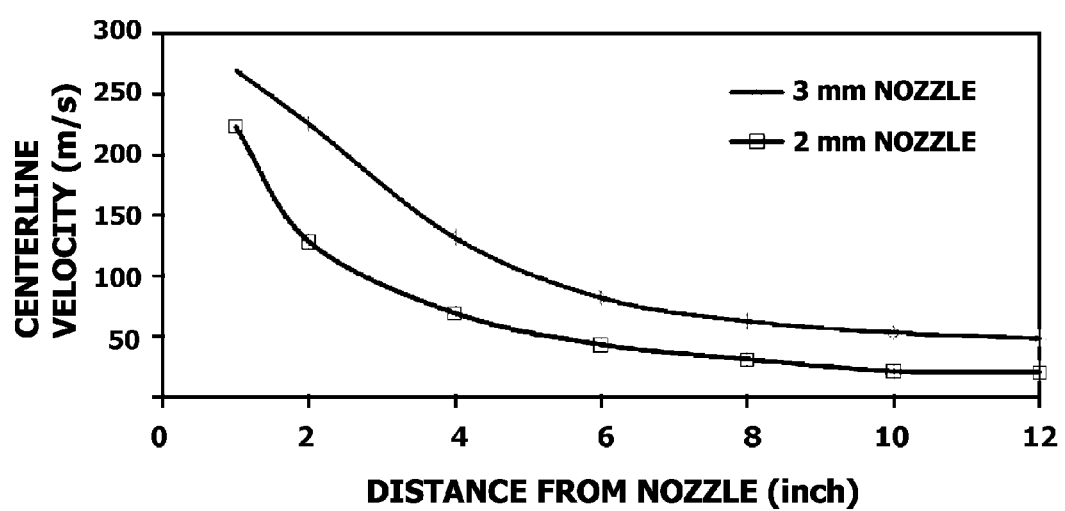
FIG. 10 is a plot showing gas jet velocity as a function of distance from nozzle.
Figure 11:
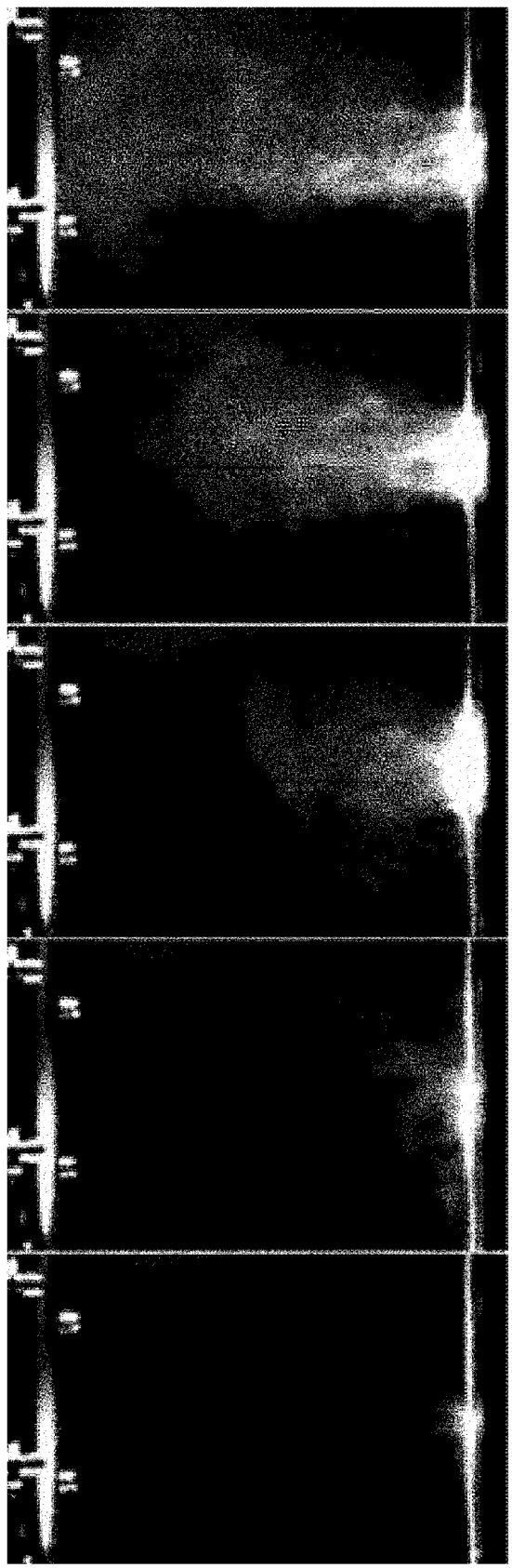
FIG. 11 is time lapse pictogram depicting re-aerosolization and entrainment of particles into a suction return stream following discharge of a gas jet pulse onto a particle-coated external surface.
Figure 12:
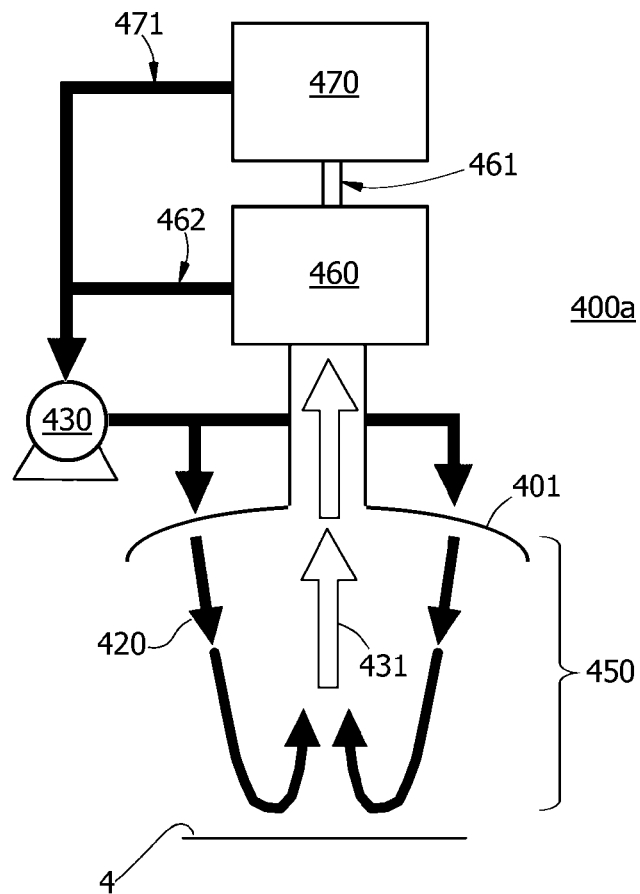
FIG. 12 is a schematic of a closed-loop device for capturing particulate residues from an interrogated surface.

The effect of pulse duration and pulse separation is analyzed in FIGS. 7 and 8. Sampling efficiency may be viewed as an exercise in optimization of two processes, the process of entrainment of residues associated with the interrogated surface in the gas streamlines (i.e. the process of removing residues from the surface) and the process of capturing those vapors and particulate residues in the inlet stream. The processes compete because excessive velocities of particles kicked up by the gas jets can propel them out of the sampling cone. Thus the overall sampling efficiency $\eta_S$ is by the equation:

$$\eta_S = \eta_R * \eta_A,$$

where $\eta_S$ is the product of two efficiencies, the removal efficiency $\eta_R$ and the aspiration efficiency $\eta_A$.

In FIG. 7 the effect of pulse duration is shown to have a paradoxical effect on particle aspiration efficiency $\eta_A$ of an eight-jet sampling head. The upper curve (dashed line) shows the timecourse for particle capture following a 10 ms jet pulse; the lower curve (dotted line) compares the timecourse for a 100 ms pulse. With longer pulse duration, particle aspiration efficiency drops due to loss of particles from the sampling cone.

However, when corrected for removal efficiency, overall efficiency is shown in FIG. 8, where particle sampling efficiency $\eta_S$ is plotted as a function of jet pulse duration, showing the combined contributions of the dislodgement process and the aspiration process. For each condition, suction flow is commenced before triggering of the gas jet pulse and is sustained after termination of the pulse. Thus pulse duration is optimized by supplying sufficient time for aggressive scouring of the surface but using a minimal time to avoid loss of agitated particles from the containment zone.

Supplemental means for dislodging particles and volatile residues in the sampling cone include pulsatile flow regimes as described by Ziskind (Gutfinger C and G Ziskind 1999. Particle resuspension by air jets—application to clean rooms. J Aerol Sci 30:S537-38, and Ziskind G et al. 2002. Experimental investigation of particle removal from surfaces by pulsed air jets. Aerosol Sci Tech 36:652-59), ion plasmas directed through the sampling jets, liquid or solvent directed through the sampling jets, or shock waves directed from the sampling head. The gas in the loop may also be heated or humidified to improve performance. If desired, the jet nozzle array may be operated in continuous mode, for example for sampling of a continuously moving belt.

FIG. 9 visually depicts the dynamic action of the interrogation jets. An array of eight jets can be seen to fire in synchrony in this graphical illustration. The appearance of the jets is enhanced by the introduction of particles in the gas flows which appear as the fine white pixilation against a black background. The duration of the pulse is about 20 milliseconds, during which high speed jet flow is clearly visible.

FIG. 10 plots jet velocity versus distance from the nozzle orifice. The jet flow velocities of the apparatus of FIG. 9 were measured by heated wire anemometry. The jets maintain a well defined linear core velocity for up to twelve inches away from the nozzle. Synchronous pulses having a centerline nozzle velocity of about Mach 0.3 are achieved. Supersonic pulses are also conceived. Flow rates of 500 sLpm or greater are achieved. Pulses of 5 ms may be actuated as frequently as every 20 ms if desired using current technology.

FIG. 11 is a time lapse view of a jet pulse/suction cycle. In this graphical illustration, a time lapse view of the action of the array of gas interrogation jets on a field of particles on a solid surface is shown. The stationary nozzles are visible at the top of the image and a thin horizontal line of the solid surface is visible at the bottom of the image. Frames are taken at 5, 7, 11, 16 and 26 milliseconds, as shown here from left to right, where the explosion of particle dust as the pulse propagates against the solid surface is clearly visible. In the later frames, a plume of particulate is seen to rise and be channeled by a suction pressure into the central collection intake at the top of the image.

The invention is also conceived as an apparatus combining functional elements needed for vapor and particle collection and analysis. FIG. 12 depicts a schematic of a particle sampling apparatus (400*a*) with housing (401, represented schematically), particle concentrator (460) and particle trap (470). Gas containing residues and aerosols is collected in the intake (431) routed to the particle concentrator. Aerodynamic lenses for example organize aerosols into a laminar stream consisting of a particle depleted sheath flow and a particle-rich core flow, which are separated by a skimmer into what are commonly termed the "minor flow" and "bulk flow", where the minor flow contains most of the particles exceeding a particular cut size. A flow split is established whereby part of the gas flow, the "minor flow" (461) enriched for particles, is directed to the particle collector or trap (470). The particle depleted "bulk" or "major" flow (462) is diverted, typically by use of a skimmer, and is ducted instead directly to the suction pressure pump. All the gas exhausted from the concentrator and the gas exhausted from the particle trap are returned to a common suction pressure source for recirculation through the sampling head. As shown in this example, the pressurized exhaust from the vacuum pump or blower (430) is used to drive sampling jets (420) forming the virtual sampling chamber (450). Particles resident on the interrogated surface (4) are dislodged and drawn into the sampling head. Material in the particle trap is periodically analyzed in situ by methods known in the art, or archived for example by removal of a filter cartridge for later analysis by chemical, biochemical or physical methods. Separate pumps may be used for out-flow and suction in-flows if asymmetric flow rates are desired. Gas flows may be filtered or purified before re-use if desired.

"Particle concentrators" include aerodynamic lens particle concentrators, aerodynamic lens array concentrators, and micro-aerodynamic lens array concentrators, when used in conjunction with a virtual impactor, skimmer or other means for separating a gas flow into a particle-enriched core flow (also termed "minor flow") and a "bulk flow", which is generally discarded. Also included are cyclone separators, ultrasound concentrators, and air-to-air concentrators generally for generating a flow split, where the "flow split" refers to the ratio of the minor flow to the bulk flow or total flow. The particle-enriched gas stream is delivered to an outlet of the aerosol concentrator module and may be conveyed to an aerosol collector module (or "particle trap", see below). Aerodynamic lens or lenses may be disposed as arrays as described in U.S. Pat. No. 7,704,294 to Ariessohn, which is co-assigned, or may be of annular geometry as described in FIGS. 17-18. Particle concentrators are also described for example in U.S. patent application Ser. No. 12/125,458 (titled "Skimmer for Concentrating an Aerosol") which is co-assigned and is hereby incorporated in full by reference.

"Particle traps" or "particle collectors" include inertial impactors, including centrifugal impactors, bluff body impactors and fine meshes or filters capable of capturing particles in a targeted size range. One class of particle traps comprises a progressive cutoff particle trap. Special classes of bluff body impactors include liquid impingers and plate impactors. Also included are wetted wall impactors and rotary vane impactors. Filters for particle removal include membrane filters and depth filters. Also included are electrostatic particle collectors. Particle collectors are described in U.S. patent application Ser. Nos. 12/364,672 (titled Aerosol Collection and Microdroplet Delivery for Analysis) and 12/833,665 (titled "Progressive Cut-Size Particle Trap and Aerosol Collection Apparatus"), which are coassigned and are hereby incorporated in full by reference. Particle traps also include filters, which may also be used to collect particulate material in a sampling return stream. Optionally the filter may be housed in a cassette with provision for interchanging the cassette periodically during sampling.

An apparatus with one or more combinations of vapor and particle analytical capability is also envisaged. Detectors for analysis and identification of particles or vapors are known in the art and may be selected for physical, chemical or biological analysis. Detection methods include visual detection, machine detection, manual detection or automated detection. Means for detecting include laser particle scattering, liquid chromatography (LC), high pressure liquid chromatography (HPLC), high pressure liquid chromatography with mass spectroscopy (HPLC/MS), gas chromatographic mass spectroscopy (GC/MS), gas chromatography coupled to electrocapture detection (GC-ECD), atmospheric pressure ionization time-of-flight mass spectrometry (TOFMS), ICP-mass spectrometry, ion mobility spectroscopy (IMS), differential ion mobility spectroscopy, secondary electrospray ionization—ion mobility spectrometry, electrochemistry, polarography, electrochemical impedance spectroscopy (EIS), surface plasmon resonance (SPR), fast atom bombardment spectroscopy (FABS), matrix-assisted laser desorption ionization mass spectrometry (MALDI/MS), inductively coupled plasma mass spectroscopy (ICP/MS), Raman spectroscopy (RS), FTIR, SAW spectroscopy, surface-enhanced Raman spectroscopy (SERS), laser induced breakdown spectroscopy (LIBS), spark-induced breakdown spectroscopy (SIBS), lateral flow chromatography, NMR, QR (quadrupole resonance), and so forth. Detection systems are optionally qualitative, quantitative or semi-quantitative. Also included are analytical devices such as spectrophotometers, fluorometers, laser particle counters and laser scattering devices, luminometers, photomultiplier tubes, photodiodes, nephelometers, photon counters, voltmeters, ammeters, pH meters, capacitive sensors, and so forth. Magnifying lenses, optical windows, lens flats, waveguides, and liquid waveguides, may be used to improve detection. Detection methods may also rely on molecular biological techniques such as hybridization, amplification, immunoassay, PCR, rtPCR, electroimpedance spectroscopy, ELISA, and the like. Means for detecting include "labels" or "tags" such as, but not limited to, dyes such as chromophores and fluorophores; radio frequency tags, plasmon resonance, radiolabels, Raman scattering, chemiluminescence, or inductive moment as are known in the prior art. Fluorescence quenching detection endpoints (FRET) are also anticipated. A variety of substrate and product chromophores associated with enzyme-linked immunoassays are also well known in the art and provide a means for amplifying a detection signal so as to improve the sensitivity of the assay, for example "up-converting" fluorophores. Explosives detection was recently reviewed by Moore (Moore, D S. 2007. Recent advances in trace explosives detection instrumentation. Sens Imaging 8:9-38).

Figure 13:
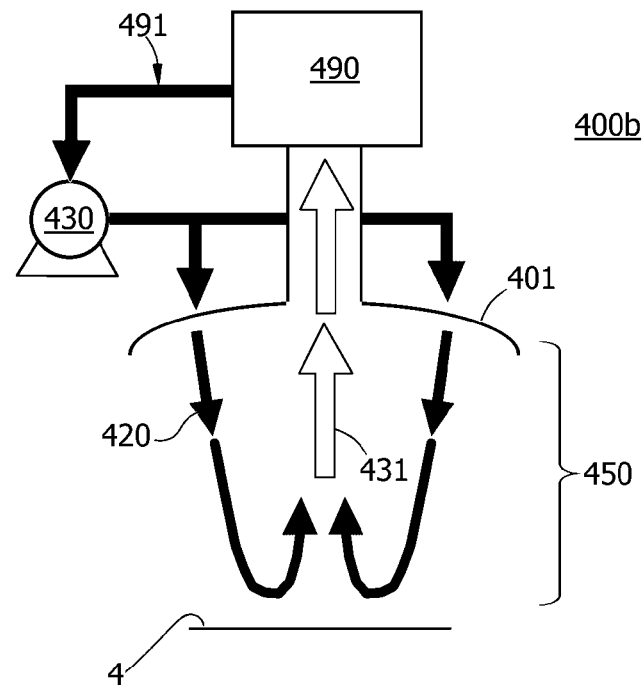
FIG. 13 is a schematic of a closed-loop device for capturing vapor residues from an interrogated surface.

FIG. 13 depicts a schematic for one embodiment (400b) of a vapor sampling apparatus with vapor trap (490) and housing (421). As shown, a virtual sampling chamber (450) is formed by gas jets (420) and a suction return stream (431) to the vapor trap. Vapor may be trapped, for example, as a condensate or by solid phase adsorption. A pump (430) recirculates the gas or air at the desired flow rate, with the linear velocity determined by the size of the jet orifices. The sampling head is held at a stand-off distance from the interrogated surface (4). Material collected in the vapor trap is periodically removed or volatilized in situ for analysis by methods known in the art such as flash heating, ultrasound, or fast atom bombardment.

Figure 14:
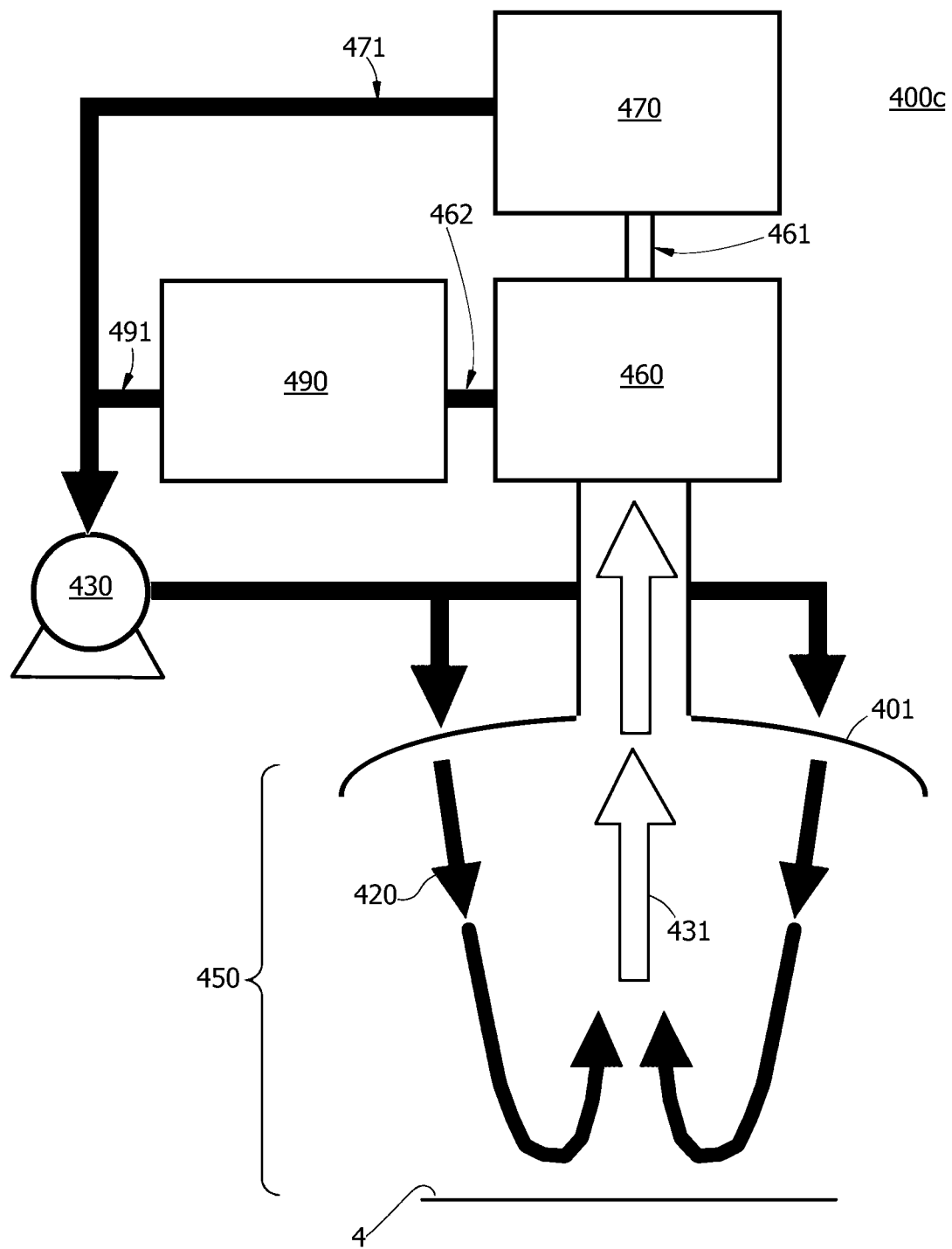
FIG. 14 is a schematic of a closed-loop device for capturing particulate and vapor residues from an interrogated surface.

FIG. 14 is a schematic of an apparatus (400c) for capture of vapors and particles. Vapors associated with a particle fraction in the particle trap (470) and vapors that escape the particle concentrator (460) in the bulk flow (462) are captured in a vapor trap (490) before the gas is recycled through vacuum/blower (430) and propulsed through the housing (401) as gas jets (420) into the virtual sampling chamber (450). Minor flow (461) from particle concentrator (460) is routed to the particle collector (470) and exhaust gas (471) is recycled through the vacuum/blower, essentially as a closed loop system, where there is a mass balance between jet inflow gas and suction return stream (431) gas recovered from the virtual sampling chamber.

In one embodiment, particularly directed at detection of trace residues of explosives, the invention combines vapor and particle trapping. Equilibrium vapor pressures of explosive materials range widely, from over $4.4 \times 10^{-4}$ Torr for nitroglycerin (which is considered to be a relatively volatile explosive), $7.1 \times 10^{-6}$ Torr for TNT, to $1.4 \times 10^{-8}$ Torr for PETN and $4.6 \times 10^{-9}$ Torr for RDX at 25° C. [source: Conrad F J. 1984. Nucl Mater Manage 13:212]. Also to be considered, however, is the affinity of the vapor molecules for solid surfaces, which may suppress free vapor concentrations, thus reducing detectable thresholds. We find that detection of volatile compounds such a dinitrotoluene, a model substance for explosives detection which has an affinity for solid surfaces, can be improved by collecting particles that have equilibrated with vapors of the explosive. These particles are typically endogenous materials that are exposed to the explosive residues in the environment, for example road dust, silica, ceramic, clay, squamous epithelial cells, hairs, fibers, and so forth.

Figure 15:
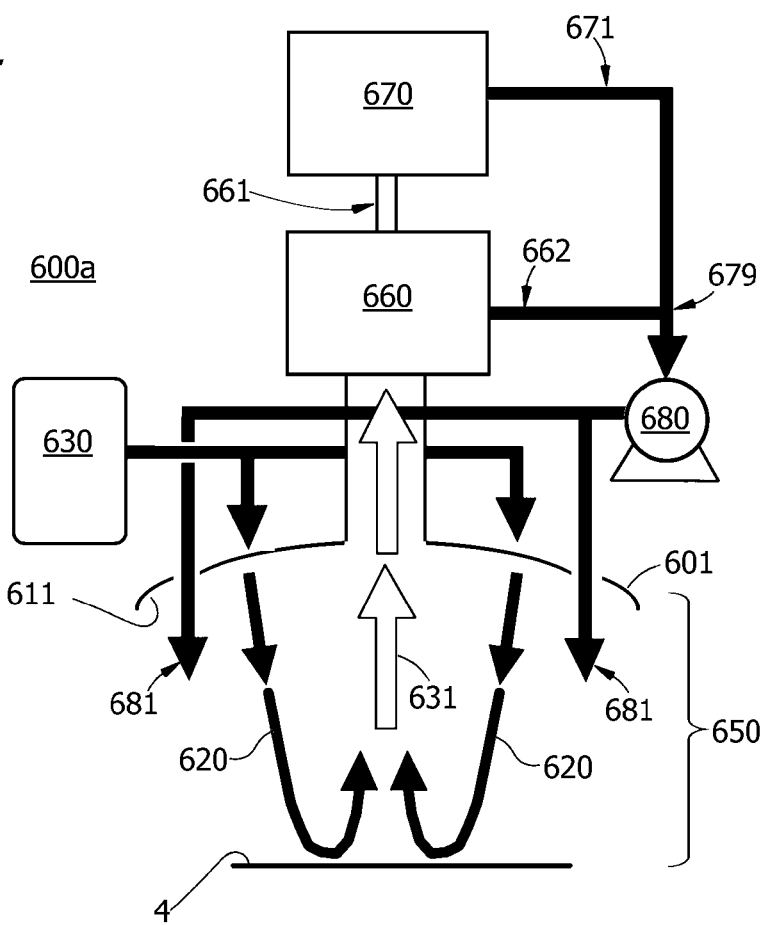
FIG. 15 is a schematic of an open-loop device with curtain wall for capturing particulate residues from an interrogated surface.
Figure 16:
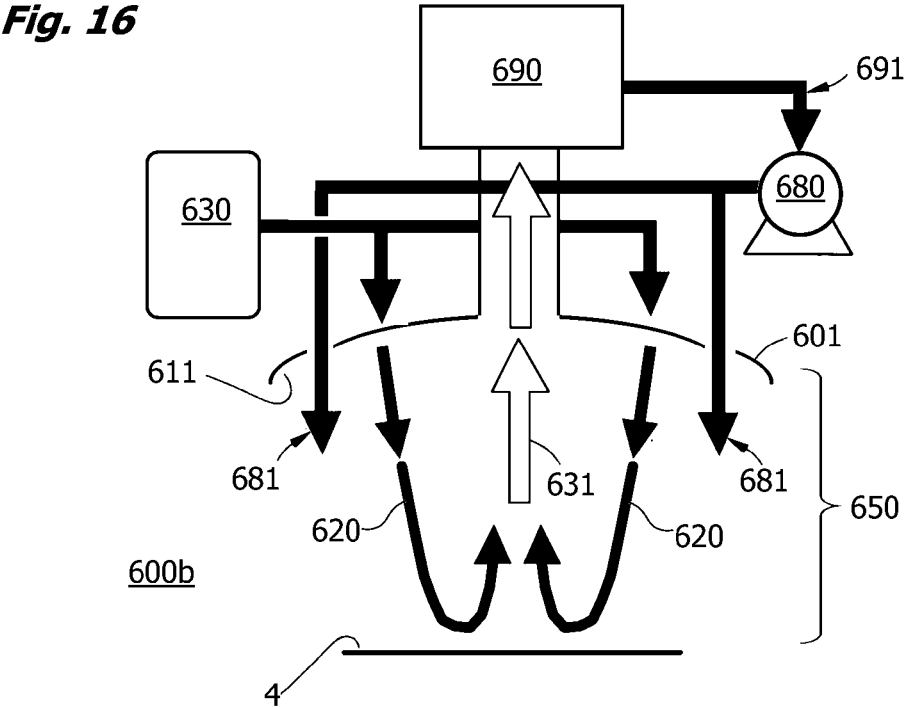
FIG. 16 is a schematic of an open-loop device with curtain wall for capturing vapor residues from an interrogated surface.

FIGS. 15 and 16 are schematics of pressurized pulse-driven devices (600a,600b) augmented with curtain wall flow for capturing particles or vapors from an interrogated surface (4). In FIG. 15, the sampling head (601) comprises a suction pump/blower (680) that draws suction return flow (631) from a central collection duct through a particle concentrator module (660) and a particle trap (670) in series. Major flow (662) and minor flow (671) are recombined as a single stream (679) for return to the suction pump as make up air. The suction pump exhaust is ducted to slit apertures on the outer perimeter of the sampling head. The slit apertures form a peripheral annulus outside the array of jet nozzles on the forward face (611) of the sampling head (601). These outermost slit apertures generate a curtain wall of flow (681) that surrounds and forms an apron around the virtual sampling chamber (650). The virtual sampling chamber is formed by pulsatile jet flows (620) from a pressurized air source (630), here shown as a 20 psig tank, although other pressures and pressure sources have been found to be useful. In this configuration, the virtual sampling chamber is enclosed in the peripheral flow of the curtain wall but the sampling jets are pulsatile in nature. Single pulses or trains of pulses may be used. Generally the curtain air is continuously ON while sampling is pulsatile, but other suction regimes may be useful.

FIG. 16 shows a corresponding sampling head (601) for collection of vapors, where air captured in the suction return flow (631) by the central collection duct is passed through a vapor trap (690) before being returned (691) to the suction/blower (680) and exhausted as curtain wall flow (681) through a peripherally disposed circumferential array of slits. Jet gas (620) is supplied from a pressurized tank (630).

Figure 17:
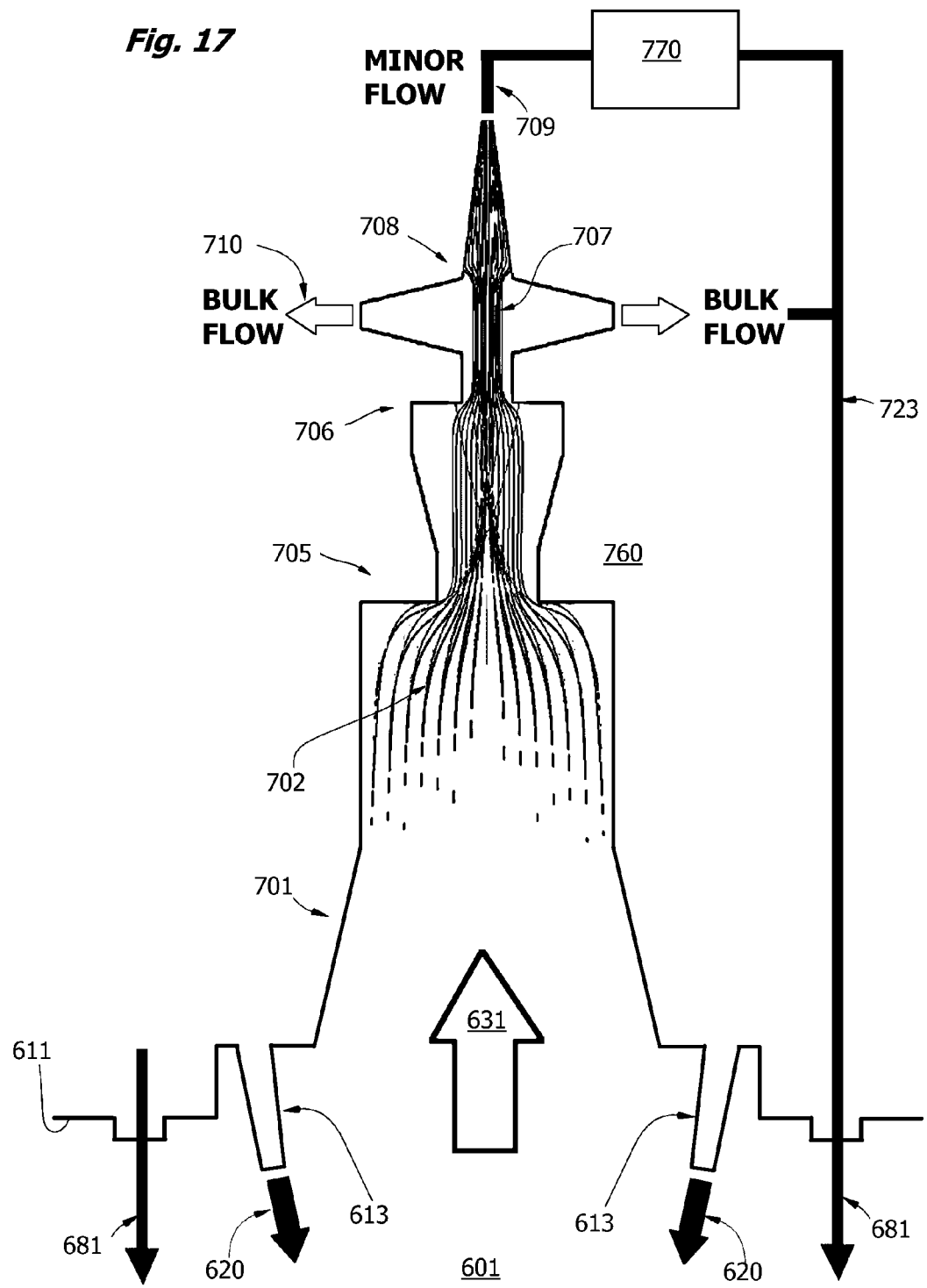
FIG. 17 is a schematic showing a device with aerodynamic lens and skimmer integrated into a sampling head.

FIG. 17 depicts a cross-sectional view of a combination "sniffer head" and particle concentration device with annular aerodynamic lenses (705,706). Unlike slit-type aerodynamic lenses, these lenses are cylindrical in cross-section. A curtain wall flow (681) from annular slit nozzles disposed on the forward face (611) of the sampling head is used to enclose a virtual sampling chamber. Interrogation jets (620) are fired from nozzles (613) as pulsatile flow at a surface beneath the sampling head (not shown). Air within the virtual sampling chamber is carried into a suction intake member (701) so that any entrained particulate or vapor material in the suction return stream (631) is captured and drawn under suction through a particle concentrator (760). The particle concentrator shown here is comprised of a two-stage aerodynamic lens assembly (705,706) and a virtual impactor (708, "skimmer"). Particle tracks (702) are shown to be focused by the aerodynamic lenses so as to form a particle-enriched core flow (707) surrounded by a particle depleted sheath flow. The core and sheath are separated in the skimmer: sheath flow is diverted as "bulk flow" (710) and the particle rich core flow (707) continues through collection duct and exits the concentrator as the "minor flow" (709). The degree of concentration is determined by the flow split between bulk and minor flow. The characteristics of the concentrator also determine a cut-size (as aerodynamic diameter) and an upper and lower range of particles that are excluded or lost from the minor flow. The configuration can be varied so that the cut size is in the range of 10 microns or lesser, for example, as is useful for a variety of applications. The minor stream may be directed through a particle trap or filter cartridge (770), and the exhaust is recycled (723) through the suction/blower (not shown) and used to generate the curtain wall flow (681).

Surprisingly, jet pulses of several milliseconds can be superimposed on curtain flow and suction cycles of one to several seconds, during which the flow regime conforms to the conditions required for use of stacked aerodynamic lenses as shown.

Figure 18:
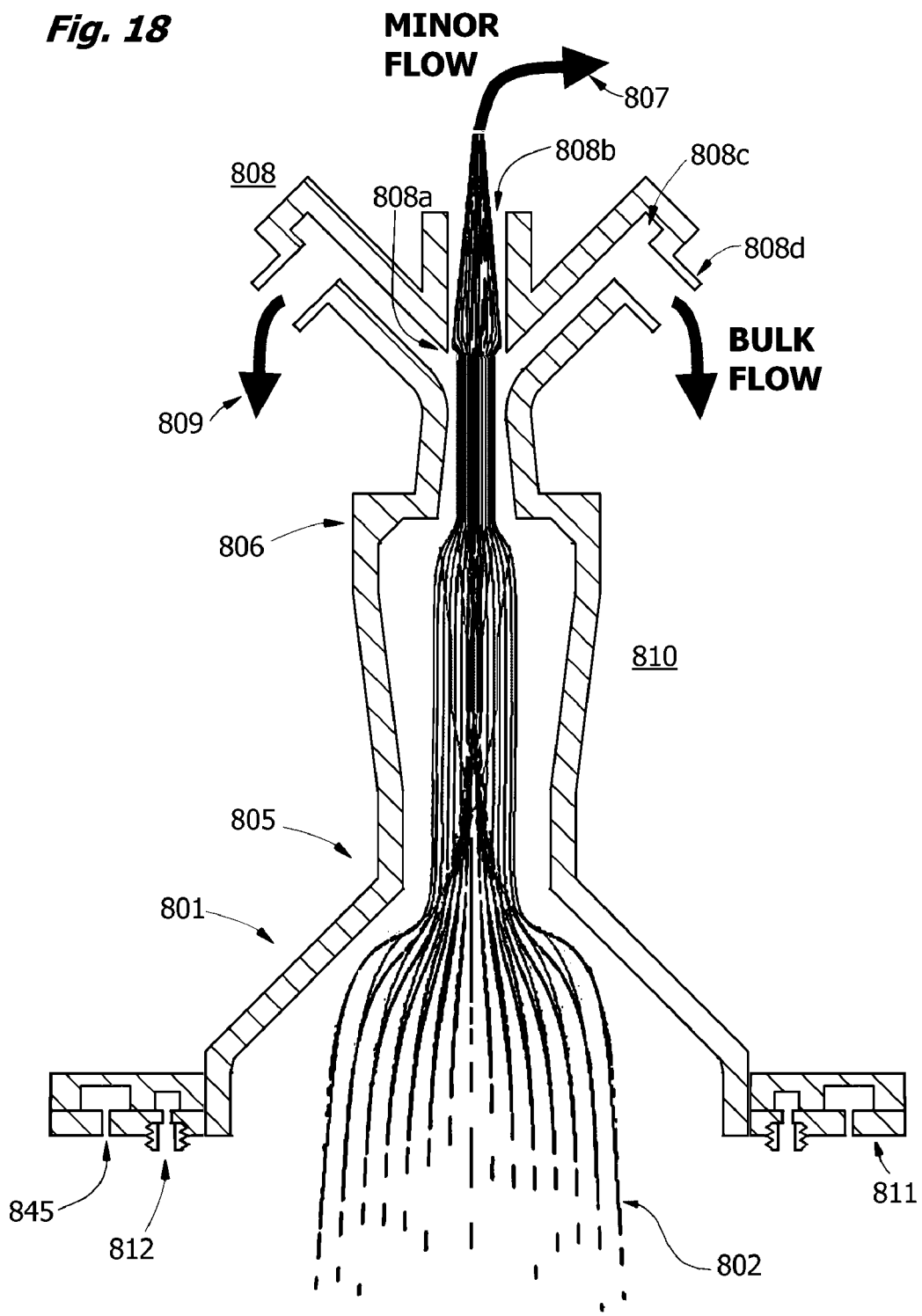
FIG. 18 shows an aerodynamically contoured device in cross-section view with annular aerodynamic lens and skimmer integrated into the sampling head at the suction intake.
Figure 19:
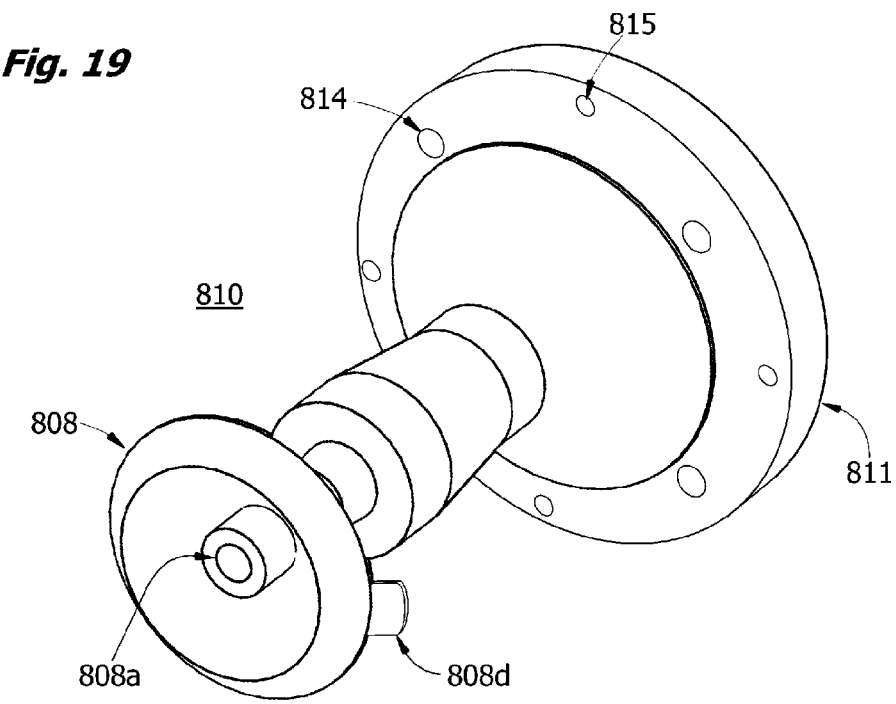
FIG. 19 is a perspective view of the sampling head of FIG. 18.
Figure 20:
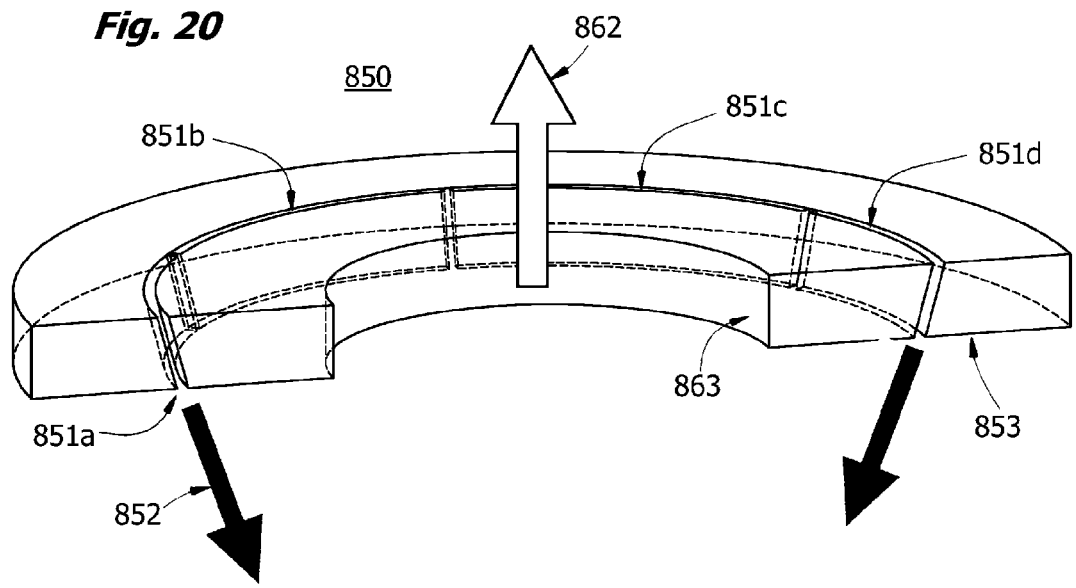
FIG. 20 is a cutaway CAD view of a jet nozzle array with slit geometry.
Figure 21:
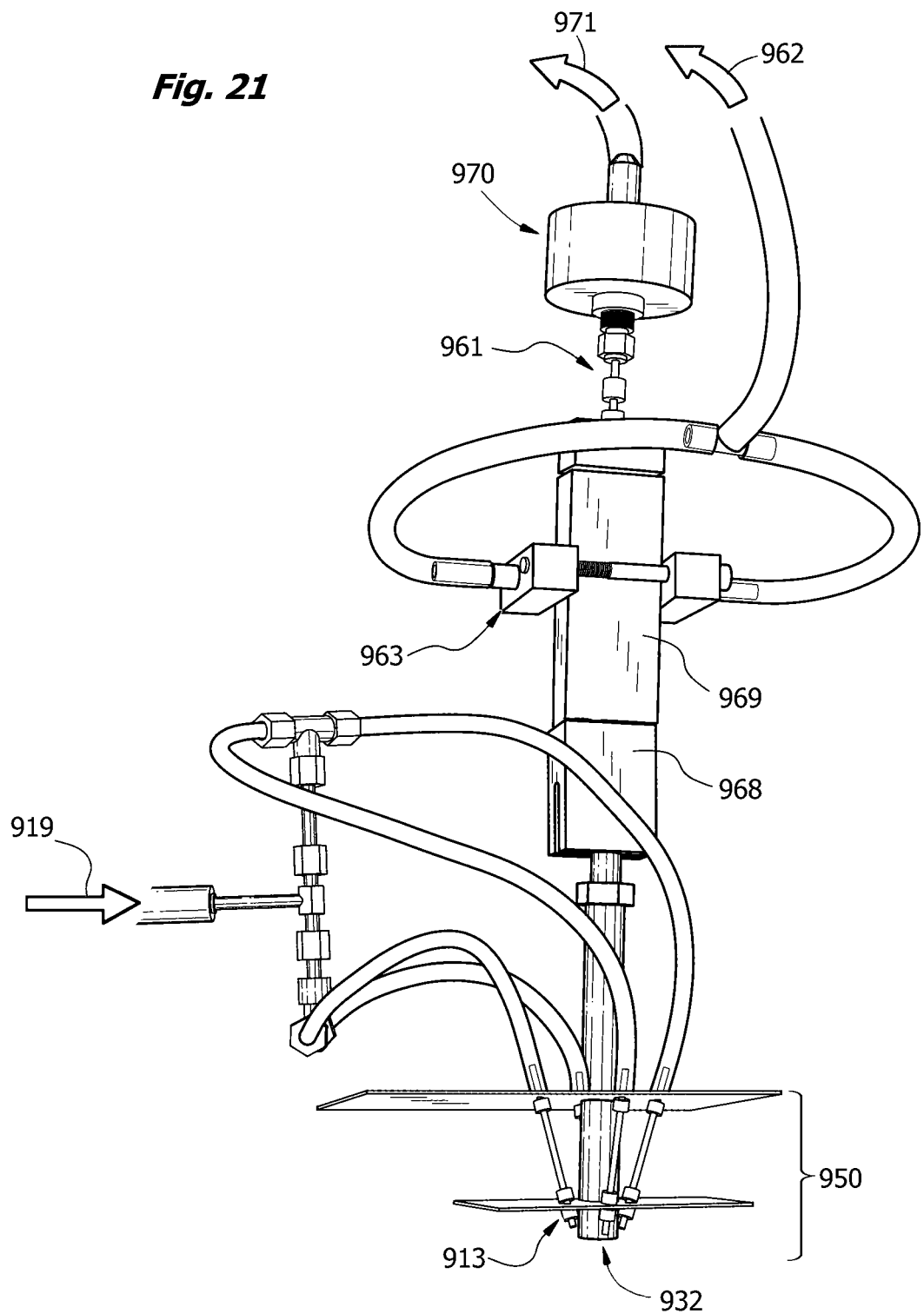
FIG. 21 is a four-jet device.

FIG. 18 depicts a cross-sectional view of a combination sampling head and particle concentration device with suction intake having a generally conical geometry (801). As shown here, the intake bell receives a particle-loaded suction return flow and focuses particle tracks (802) in a pair of aerodynamic lenses (805,806). A virtual impactor (808) is used to separate minor flow (807) and bulk flow (809). Minor flow is channeled to a particle concentrator and then recombined with major flow for recycling to curtain wall flow (681). As described previously, the sniffer head consists of a forward face (811) with jet nozzles (812), annular slit nozzles (845) and a central suction intake member (801).

The virtual impactor (808) is comprised of a skimmer mouth (808*a*), a central collection duct (808*b*), a discoid chimney duct (808*c*) for routing the bulk flow (809) to nipples (808*d*) adapted, as shown here, for a hose connection to a vacuum source.

Multiple aerodynamic lenses may be used. For example by stacking four lenses, concentration of particles over a broad range of particle sizes can be achieved. Beginning with the first lens, which acts on larger particles, the remaining lenses in the stack progressively act on smaller particles in steps of 2× to 4×. Thus by example, a four lens stacks may focus particles of 100, 30, 10, and 5 microns respectively, while not limited thereto.

In order to increase particle velocities in the central collection duct and reduce elutriative effects, the intake duct geometry may be aerodynamically shaped to minimize particle impact, for example as per a NACA duct, Laval duct, elliptical duct intake, bell shaped duct intake, parabolic horn intake, exponential horn intake, quadratic convergent duct intake, power series convergent duct intake, or other tapered geometry of the intake. Designs are created by trial and error with a sprinkling of intuition. Fins or airfoils may be used to minimize the turbulence, reduce deadspace and increase linear velocities of the streamlines may also be used. As the lenses are improved by contouring to relieve eddy separation and particle wall impaction, performance is also seen to improve significantly, particularly in the collection of larger particles, which problematically are otherwise found to be lost to sedimentation and rebound following wall impaction in the sampling head and concentrator.

FIG. 19 is a CAD drawing of the combination sampling head and annular aerodynamic lens with skimmer assembly of FIG. 18. The sampling face (810) of the intake bell is pointed away from the viewer in this case so that the discoid skimmer assembly (808) is more clearly depicted. A central collection duct (808*a*) and hose nipple (808*d*) are labelled. Also shown are mounting points on the lower sampling head for gas jet feed (814) and for curtain air slot feed (815).

FIG. 20 is a cutaway CAD view of a jet nozzle array with slit geometry. Here the architecture of the jet nozzles is modified and integrated into the material of the sampling head (850). The forward face (853) of the sampling head is configured for emitting fan-shaped jets (852) via a ring of slits (851*a,b,c,d*). Central suction intake port (863) for receiving sampling flow stream (862) is shown in cutaway view, where the front half of the sampling head is not shown.

FIG. 21 depicts a working sampling head with particle concentrator. In this example, a filter cartridge (970) is used as a particle trap, but the technology is not limited thereto. Of utility are the μADL aerosol concentrators and particle traps (U.S. patent application Ser. Nos. 11/597,075; 12/125,458; and 12/364,672, co-assigned) developed in our laboratory, which have particle cutoff sizes of less than 1 micron, and also centrifugal particle traps we have reported elsewhere. In the apparatus as shown, the four sampling jet nozzles (913) of the sampling head are fed with compressed air (919) through a flow splitting manifold. The sampling jets are mounted in a pair of plates of the sampling head (950) lowermost in the drawing so as to configure the jets with a fixed impingement angle. At the center of the four sampling jets is a vertical suction collection tube (932) extending upward through the plates and into a block which serves as an adaptor (968) to interface with a virtual impactor-type particle concentrator (969). Minor flow is routed to the filter cassette (970) via tabulation means (961). The major or bulk flow from the internal skimmer section (not shown) is exhausted through the pair of manifolds (963) laterally mounted on the virtual impactor, which are connected (962) to a vacuum source during operation. Also connected to vacuum is the nipple topmost in the figure, which is connected (971) to the vacuum source powering the filter cartridge where the particle sample accumulates.

A number of methods may be used to augment the capacity of the sampling head to strip off particles and vapor residues from surfaces or objects. One such technique is pulsatile flow. Feeding the sampling nozzles with pulsed gas at about 100 to 200 Hz results in improved particle dislodgement and lift-off at most linear jet velocities.

Alternatively, the gas feed may be ionized by contact with a source of ions, such sources including but not limited to a "corona wire," a source of ionizing radiation, a glow discharge ionization source, or a radio-frequency discharge. The ionized gas stream is used to neutralize electrostatic associations of particles with surfaces and improve lift off of particles.

The sampling jets may also be supplemented with higher molecular weight gases include water, argon, xenon, fluorocarbons, carbon dioxide, sulfur hexafluoride, tert-butane, and solvent vapors such as isopropane, methyl-tert-butyl ether. Collisions of higher molecular weight gas atoms or molecules results in improved evaporation of volatile residues. The carrier is typically air, argon or nitrogen and the gas or solvent is a high molecular weight molecule sufficient to aid in dissociation of particles and volatile residues from the object or environmental surface of interest. The presence of solvent vapors also can aid in volatilizing dry chemical residues such as explosives and water will compete with organic molecules for binding to solid substrates.

EXAMPLES

In a first example, fluorescent micron-sized latex beads were dispersed on a surface and a quad-jet nozzle with suction intake was directed at the surface. A flow rate of less than 100 m/sec from the gas sampling jets and balanced uptake through the central suction intake resulted in particle entrainment in the suction intake as evidenced by fluorescent particle capture on an in-line filter membrane. Inspection of the filter membrane by epifluorescence microscopy revealed characteristic fluorescent latex beads and small aggregates of latex beads indicative of particle capture.

In a second example, tests were conducted using Ammonium Nitrate/Fuel Oil (ANFO) explosive particles deposited on painted aluminum surfaces to determine the ability to remove these particles using directed, near-sonic air jets. ANFO was prepared by mixing reagent grade ammonium nitrate sieved through a 300 micron mesh with premium diesel fuel at a ratio of 1 gram to 80 microliters. Particles were applied to black enamel painted aluminum coupons by dipping a finger into the ANFO mixture, placing the finger in contact with the painted surface, and allowed to dry overnight. Significant fractions of ANFO residue were aerosolized using air jets; removal efficiency increases with the duration or frequency of application of the air jet, with increasing air jet velocity, and as a function of the impingement angle.

In related experiments, near instantaneous >90% removal of ASHRAE 52.1 dust was demonstrated at jet velocities of 40 m/s or less [Consists of Arizona Road dust (72%), Carbon Black (23%), and Cotton Linters (5%)] using a jet blower at an angle to a glass surface, over a range of 1-6 inches from surface.

In a third example, ASCO valves having a five to ten millisecond response time were used to control firing of an eight jet array. Jet pneumatic pressure was supplied from a buffered compressed gas reservoir precharged to 20 psig. Jet pulses were on the order of 0.1 to 1 liter per pulse for a working device. Jet nozzles were tilted 7.5 degrees toward the apex of a virtual cone extending from a ring of jet nozzles along the centerline long axis of the head. An Ametek blower operating at about 600 sLpm was used to generate a suction pressure at the collector inlet, which was generally conical in shape. Exhaust from the blower was filtered and used for curtain air, which was balanced. An in-line filter disk was mounted at the head of the collector inlet to trap entrained particles derived from fingerprints applied to the surface. Satisfactory results were obtained by distancing the head about six inches from a surface charged with foreign matter, priming the suction pump and air curtains at time zero, activating a 10 to 20 millisecond pulse from the jets at time zero plus 0.5 seconds, and then terminating suction pressure about two seconds after initiation of the pulse cycle. Examination of the filter disk revealed trapped particles in the range of 10 to 200 microns in aerodynamic diameter.

While the above is a complete description of selected embodiments of the present invention, it is possible to practice the invention use various alternatives, modifications, combinations and equivalents. All of the U.S. patents, U.S. patent application publications, U.S. patent applications, foreign patents, foreign patent applications and non-patent publications referred to in this specification are incorporated herein by reference in their entirety. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A device for sampling residues from an external surface of an object, structure, vehicle or person, which comprises:
    a) a sampling head with forward face and perimeter;
    b) a suction intake port disposed centrally on said forward face and an array of jet nozzles peripherally disposed on said forward face around said suction intake port, wherein said jet nozzles are directed at a virtual apex of a virtual cone with base resting on said forward face;
    c) a positive pressure source for firing a gas sampling jet with streamlines from each nozzle of said array of jet nozzles;
    d) a suction pressure source for drawing a sampling return stream of gas into said suction intake port, said suction pressure source having an inlet and an outlet;
    wherein said streamlines of said gas sampling jets are directed toward said virtual apex of said virtual cone, said streamlines tracing an involuted frustroconical "U" under the attraction of said suction pressure source and converging with said sampling return stream at said suction intake port along a central axis of said virtual cone when impinging on said external surface.

2. The device of claim 1, wherein said gas sampling jet and sampling return stream form a virtual sampling chamber having said gas sampling jets directed linearly along the walls of said virtual cone and said sampling return stream directed along said central axis of said virtual cone, and further wherein said involuted frustroconical "U" fluidly connects said gas sampling jets and said sampling return stream at a virtual frustrum of said virtual cone when impinging on said external surface.

3. The device of claim 2, wherein each said gas sampling jet is fired as a pulse or train of pulses and said array of jet nozzles is fired in synchrony.

4. The device of claim 3, wherein said suction pressure source is operated before and after firing said gas sampling jet.

5. The device of claim 3, wherein said virtual cone has a height $D_c$ and an apex angle theta, and further wherein said virtual frustrum of said virtual cone is formed with a height $D_f$, said height $D_f$ being less than $D_c$.

6. The device of claim 3, further comprising an annular slit array for forming a curtain wall of gas disposed as an apron around said sampling head, wherein said gas of said curtain wall is an exhaust discharged from said suction pressure source outlet.

7. The device of claim 1, further comprising a particle concentrator for concentrating a particulate aerosol in said sampling return stream, wherein said particle concentrator is disposed in said sampling return stream between said suction intake port and said suction pressure source inlet.

8. The device of claim 7, wherein said particle concentrator comprises an annular aerodynamic lens and a skimmer, said skimmer having a minor flow outlet and a bulk flow outlet.

9. The device of claim 8, further comprising a vapor trap for collecting a volatile residue in said sampling return stream, wherein said vapor trap is disposed in said sampling return stream between said bulk flow outlet and said suction pressure source.

10. The device of claim 1, further comprising a particle collector for collecting a particulate aerosol in said sampling return stream, wherein said particle collector is disposed in said sampling return stream between said suction intake port and said suction pressure source inlet.

11. The device of claim 10, wherein said particle collector is a filter.

12. The device of claim 10, wherein said particle collector is an inertial impactor, a centrifugal impactor, a liquid impinger, a cyclone, a wetted wall cyclone, a filter, a rotating vane impactor, or an electrostatic particle trap.

13. The device of claim 1, further comprising a vapor trap for collecting a volatile residue in said sampling return stream, wherein said vapor trap is disposed in said sampling return stream between said suction intake port and said suction pressure source inlet.

14. The device of claim 1, wherein said sampling head is portable or is robotically operated.

15. A method for sampling a residue from an exterior surface of an object, structure or person, which comprises contacting said virtual sampling chamber of claim 2 with an exterior surface at a distance less than the height of said virtual cone, whereby residues from said external surface are swept into said sample return stream by said streamlines.

16. The method of claim 15, wherein each said gas sampling jet is fired as a pulse or train of pulses and said array of jet nozzles is fired in synchrony, said pulse or pulses having a pulse duration of less than or about 1000 milliseconds, more preferably 10 to 100 milliseconds.

17. The method of claim 15, wherein said gas sampling jets have a centerline nozzle velocity of about Mach 0.3 or greater.

* * * * *

UNITED STATES PATENT AND TRADEMARK OFFICE
CERTIFICATE OF CORRECTION

PATENT NO. : 8,307,723 B2  Page 1 of 1
APPLICATION NO. : 12/834860
DATED : November 13, 2012
INVENTOR(S) : Igor V Novosselov et al.

It is certified that error appears in the above-identified patent and that said Letters Patent is hereby corrected as shown below:

On the Title Page, Item (56) "References Cited" under US PATENT DOCUMENTS (continued), to include:

-- 2009/0084201   A1   4/2009 Almirall --.

Signed and Sealed this
Twenty-ninth Day of April, 2014

Michelle K. Lee
*Deputy Director of the United States Patent and Trademark Office*